(12) United States Patent
Peled et al.

(10) Patent No.: US 11,746,325 B2
(45) Date of Patent: *Sep. 5, 2023

(54) SELECTION AND USE OF UMBILICAL CORD CELL FRACTIONS SUITABLE FOR TRANSPLANTATION

(71) Applicant: Gamida Cell Ltd., Jerusalem (IL)

(72) Inventors: Tony Peled, Mevaseret Zion (IL); Einat Galamidi Cohen, Modiin (IL); David Snyder, Moshav Bnei Dror (IL)

(73) Assignee: Gamida Cell Ltd. (IL)

( * ) Notice: Subject to any disclaimer, the term of this patent is extended or adjusted under 35 U.S.C. 154(b) by 900 days.

This patent is subject to a terminal disclaimer.

(21) Appl. No.: 16/614,057

(22) PCT Filed: May 16, 2017

(86) PCT No.: PCT/IL2017/050551
§ 371 (c)(1),
(2) Date: Nov. 15, 2019

(87) PCT Pub. No.: WO2018/211487
PCT Pub. Date: Nov. 22, 2018

(65) Prior Publication Data
US 2020/0172863 A1 Jun. 4, 2020

(51) Int. Cl.
| C12N 5/078 | (2010.01) |
| A61P 7/00 | (2006.01) |
| A61P 31/00 | (2006.01) |
| A61P 35/02 | (2006.01) |
| A01N 1/02 | (2006.01) |
| A61K 35/51 | (2015.01) |

(52) U.S. Cl.
CPC .......... *C12N 5/0634* (2013.01); *A01N 1/0284* (2013.01); *A61K 35/51* (2013.01); *A61P 7/00* (2018.01); *A61P 31/00* (2018.01); *A61P 35/02* (2018.01)

(58) Field of Classification Search
CPC ..... C12N 5/0647; C12N 5/0665; A61K 35/51
See application file for complete search history.

(56) References Cited

U.S. PATENT DOCUMENTS

| 7,955,852 | B2 | 6/2011 | Peled et al. |
| 8,846,393 | B2 | 9/2014 | Peled |
| 8,986,992 | B2 | 3/2015 | Peled |
| 2012/0093782 | A1 | 4/2012 | Grove et al. |
| 2012/0141434 | A1 | 6/2012 | Peled et al. |
| 2015/0050730 | A1 | 2/2015 | Cabral et al. |
| 2020/0138871 | A1 | 5/2020 | Peled et al. |

FOREIGN PATENT DOCUMENTS

| CL | 2019003231 A1 | 4/2020 |
| CL | 2019003272 | 5/2020 |
| RU | 2360965 | 7/2009 |
| WO | WO 2004/096972 | 11/2004 |
| WO | WO 2007/063545 A2 | 6/2007 |
| WO | WO 2010/128510 A1 | 11/2010 |
| WO | WO 2013/141731 A2 | 9/2013 |
| WO | WO 2016/207240 A1 | 12/2016 |
| WO | WO 2017/096347 A1 | 6/2017 |
| WO | WO 2018/211487 A1 | 11/2018 |
| WO | WO 2018/211509 A2 | 11/2018 |

OTHER PUBLICATIONS

Ebener, U. et al. (2003). CD133/CD34 Expression on Hematopoietic Stem-/Progenitor Cells and Acute Leukemic Blasts. In: Berdel, et al. (eds) Transplantation in Hematology and Oncology II. Springer, Berlin, Heidelberg, https://doi.org/10.1007/ (Year: 2003).*
Lockridge et al. "Analysis of the CD1 Antigen Presenting System in Humanized SCID Mice", PLoS ONE, 6(6): e21701:1-16, 2011.
Parikh et al. "Successful Engraftment of Donor Umbilical Cord Blood (UCB) Cells After Co-Transplantation of Nicord® (Ex Vivo Expanded UCB Progenitor Cells With Nicotinamide) and A Second Unmanipulated Cord Blood Unit After Myeloablative Chemotherapy in Pediatric Patients With Severe Sickle Cell Disease", Blood, 128(22): 3651, Poster, Dec. 2, 2016.
Cotoia et al., "High Mobilization of CD133+/CD34+ Cells Expressing HIF-1a and SDF-1a in Septic Abdominal Surgical Patients", BMC Anesthesiology, Jun. 2020, vol. 20, No. 158, 8 pages.

(Continued)

*Primary Examiner* — Thane Underdahl
(74) *Attorney, Agent, or Firm* — COOLEY LLP; Ivor R. Elrifi; Matthew Pavao

(57) ABSTRACT

Methods of selecting umbilical cord blood units for ex-vivo expansion, separation of CD133+/CD34+ positive and uncultured CD133+/CD34+ negative fractions, methods for expanding the selected CD133+/CD34+ fraction, selection of expanded populations of CD133+/CD34+ cord blood cells for transplantation to subjects in need thereof and the therapeutic use of suitable selected, ex-vivo expanded CD133+/CD34+ and unselected CD133/CD34 negative cord blood fractions for transplantation in the clinical setting, for treatment of hematological malignancies are provided. The present invention also envisions kits comprising the expanded and unselected cord blood fractions.

25 Claims, No Drawings

(56) References Cited

OTHER PUBLICATIONS

Kourek et al. "Endothelial Progenitor Cells Mobilization After Maximal Exercise According to Heart Failure Severity", World Journal of Cardiology, Nov. 2020, vol. 12, No. 11, p. 526-539.
Peled T. et al. "Pre-Clinical Development of Cord Blood-Derived Progenitor Cell Graft Expanded Ex Vivo With Cytokines and the Polyamine Copper Chelator Tetraethylenepentamine", Cytotherapy, 2004, vol. 6, No. 4, p. 344-355.
Stiff et al. "StemEx (Copper Chelation Based) Ex Vivo Expanded Umbilical Cord Blood Stem Cell Transplantation (UCBT) Accelerates Engraftment and Improves 100 Day Survival in Myeloablated Patients Compared to a Registry Cohort Undergoing Double Unit UCBT: Results of a Multicenter Study of 101 Patients With Hematol", Blood, 2013, vol. 122, No. 21, p. 295-301.
Anand et al. "Transplantation of Ex Vivo Expanded Umbilical Cord Blood (NiCord) Decreases Early Infection and Hospitalization", Biology of Blood and Marrow Transplantation, BBMT, 2017, p. 1-29.
Barker et al. "Results of a Prospective Multicentre Myeloablative Double-Unit Cord Blood Transplantation Trial in Adult Patients With Acute Leukaemia and Myelodysplasia", British Journal of Haematology, Published Online 2014, vol. 168, No. 3, p. 405-412.
ClinicalTrials "Allogeneic SCT of Cordin™, in Patients With Hemoglobinopathies", ClinicalTrials.gov, NCT02504619, 2016, 3 pages.
ClinicalTrials "Pilot Study Evaluating Safety & Efficacy of a DCBT: NiCord® & UNM CBU to SCD Patients After Myeloablative Therapy", ClinicalTrials.gov, NCT01590628, 2017, 3 pages.
ClinicalTrials "Pilot Study Evaluating Safety & Efficacy of DCBT: NiCord® & UNM CBU to Patients With Hematological Malignancies", ClinicalTrials.gov, NCT01221857, 2014, 3 pages.
ClinicalTrials "Transplantation of Ex Vivo Expanded, UCB-Derived, Stem & Progenitor Cells Vs. Unmanipulated UCB for HM Patients", ClinicalTrials.gov, NCT02730299, 2016, 4 pages.
ClinicalTrials "Transplantation of NiCord®, Umbilical Cord Blood-Derived Ex Vivo Expanded Cells, in Patients With HM", ClinicalTrails.gov, NCT01816230, 2017, 4 pages.
De Lalla, et al. "High-frequency and adaptive-like dynamics of human CD1 self-reactive T cells", European Journal of Immunology, 2011, vol. 41, No. 3, p. 602-610.
Delaney C. et al. "Notch-mediated Expansion of Human Cord Blood Progenitor Cells Capable of Rapid Myeloid Reconstitution", Nature Medicine, 2010, vol. 16, No. 2, p. 17 pages.
De Lima et al. "Cord-Blood Engraftment with Ex Vivo Mesenchymal-Cell Coculture", The New England Journla of Medicine, 2012, vol. 367, No. 24, p. 2305-2315.
European Medicines Agency "EU Clinical Trials Register", European Medicines Agency, May 17, 2016, 7 pages.
Horwitz, et al. "NiCord® Expanded Hematopoietic Progenitor Cells (HPC) are Capable of Prolonged Myeloid and Lymphoid Engraftment Following Myeloablative Dual Umbilical cord Blood (UCB) Transplantation", Biology of Blood and Marrw Transplantation, Poster Session II, 18(2)/Suppl.: 326, # 328, Feb. 2012.
Horwitz, et al. "NiCord® Single Unit Expanded Umbilical Cord Blood Transplantation: Results of phase I/ II trials set the stage for a definitive phase III clinical trial", ASCO Annual Meeting 2016 presentation, 21 pages.
Horwitz et al. "Umbilical Cord Blood Expansion With Nicotinamide Provides Long-Term Multilineage Engraftment", The Journal of Clinical Investigation, 2014, vol. 124, No. 7, p. 3121-3128.
Jagasia M. et al. "National Institutes ofHealth Consensus Development Project on Criteria for Clinical Trials in Chronic Graft-versus-Host Disease: I. The 2014 Diagnosis and StagingWorking Group Report", Biology of Blood and Marrow Transplantation, 2015, vol. 21, p. 389-401.
Miltenyi Biotec, "CD133 MicroBead Kit—human-lyophilized", Data Sheet (2011) pp. 1-4. [Retrieved from the Internet Dec. 17, 2019]: https://www.miltenyibiotec.com/upload/assets/IM0002136.PDF.
Okamoto O. et al. "Common molecular pathways involved in human CD133+/CD34+ progenitor cell expansion and cancer", Cancer Cell International, 2007, vol. 7, No. 11, 12 pages.
Peled T. et al. "Nicotinamide, a SIRT1 inhibitor, inhibits differentiation and facilitates expansion of hematopoietic progenitor cells with enhanced bone marrow homing and engraftment", Experimental Hematology, 2012, vol. 40, p. 342-355.
Reader N. et al. "Analysis of the Viability of Umbilical Cord blood Stem Cells", Journal of Stem cells and Regenerative Medicine, 2009, vol. 5, No. 2, p. 44-48.
Soufizomorrod, et al. "Expansion of CD133+ Umbilical Cord Blood Derived Hematopoietic A Stem Cells on a Biocompatible Microwells", Int J Hematol Oncol Stem Cell Res. 2013, vol. 7, No. 1 pp. 9-14.
Wagner J. et al. "Phase I/II Tiial of StemRegenin-1 Expanded Umbilical Cord Blood Hematopoietic Stem Cells Supports Testing as a Stand-Alone", Cell Stem Cell, 2016, vol. 18, p. 144-155.
Scaradavou et al. "Cord Blood Units with Low CD34+ Cell Viability Have a Low Probability of Engraftment after Double Ubit Transplantation"; Biol Blood Marrow Transplant, 2010, 16(4): 500-508.
De Lima et al. "Transplantation of Ex Vivo Expanded Cord Blood Cells Using the Copper Chelator Tetraethylenepentamine: a Phase I/II Clinical Trial", Bone Marrow Transplantation, 41(9): 771-778, Jan. 21, 2008.
Flores-Guzman et al. "Concise Review: Ex Vivo Expansion of Cord Blood-Derived Hematopoietic Stem and Progenitor Cells: Basic Principles, Experimental Approaches, and Impact in Regenerative Medicine", Stem Cells Translational Medicine, 2(11): 830-838, Oct. 7, 2013.
Frisch et al. "Hematopoietic Stem Cell Cultures and Assays", Methods in Molecular Biology, 1130: 315-324, May 5, 2015.
Lysak et al. "Validation of Shortened 2-day Sterility Testing of Mesenchymal Stem Cell-based Therapeutic Preparation on an Automated Culture System", Cell and Tissue Banking 17(1): 1-9, Jul. 5, 2016.
Singh et al. "Evaluation of Four Methods for Processing Human Cord Blood and Subsequent Study of the Expansion of Progenitor Stem Cells Isolated Using the Best Method", Cytotherapy, 11(6): 768-777, 2009.
Thesaurus.com "How to Use the Slash Symbol", retrieved from the internet; published Mar. 7, 2013, 3 pages.
Woods et al. "Off the Shelf Cellular Therapeutics: Factors to Consider During Cryopreservation and Storage of Human Cells for Clinical Use", Cytotherapy 18(6):697-711, Jun. 2016.

\* cited by examiner

SELECTION AND USE OF UMBILICAL CORD CELL FRACTIONS SUITABLE FOR TRANSPLANTATION

CROSS-REFERENCE TO RELATED APPLICATIONS

This application is a National Stage Application, filed under 35 U.S.C. § 371, of Patent Application No. PCT/IL2017/050551 filed May 16, 2017, the contents of which are incorporated by reference in its entirety.

FIELD AND BACKGROUND OF THE INVENTION

The present invention relates to methods of selecting umbilical cord blood units for ex-vivo expansion, separation of CD133+/CD34+ positive and uncultured CD133+/CD34+ negative fractions, methods for expanding the selected CD133+/CD34+ fraction, selection of expanded populations of CD133+/CD34+ cord blood cells for transplantation to subjects in need thereof and the therapeutic use of suitable selected, ex-vivo expanded CD133+/CD34+ and unselected CD133/CD34 negative cord blood fractions for transplantation in the clinical setting, for treatment of hematological malignancies. The present invention also envisions kits comprising the expanded and unselected cord blood fractions.

More than two thirds of patients awaiting hematopoietic stem cell transplantation lack a suitable matched related donor, making unrelated donor grafts a necessity. Cord blood, bone marrow and other hematopoietic-rich tissues are a valuable source of stem cells, particularly where a matched unrelated donor cannot be found within a reasonable time. Advantages of the use of cord blood include the fact that it is readily available, carries less risk of transmission of blood-borne infectious diseases, and is transplantable across HLA barriers with diminished risk of graft-versus-host disease compared with similarly mismatched stem cells from the peripheral blood or bone marrow of related or unrelated donors. Another important advantage of cord blood is the rapidity with which an acceptable cord-blood unit, once identified, can be acquired.

However, a major clinical limitation of umbilical cord blood is the low stem cell dose available for transplantation, compared to mobilized peripheral blood (PB) or bone marrow. This low stem cell dose can compromise the chances of engraftment and contributes to delayed kinetics of neutrophil and platelet recovery, as well as other transplant outcomes, resulting in transplant related complications, morbidity and mortality, and longer duration of hospitalization. To address this shortcoming, several approaches have been developed, including dual umbilical cord blood transplantation (DCBT) and ex vivo expansion of cord blood stem cells. DCBT has become standard practice in cord blood transplantation for recipients in whom a single cord blood unit of adequate cell dose is unavailable.

Still, engraftment kinetics of DCBT are no better than single unit transplants. Ex vivo expansion is still an experimental approach. The aim of ex vivo expansion of cord blood is to provide a graft with sufficient numbers of cells that have rapid and robust in vivo neutrophil and platelet producing potential to enable successful transplantation. Delaney et al. (2010, Nat Med 16:232-236) and De Lima et al. (2012, N Engl J Med, 367:2305-2315) published the results of two clinical studies employing ex vivo expanded cord blood grafts in a double cord configuration, i.e., one unit used for expansion, and a second unit administered unmanipulated, reporting that although the expanded cells were observed as early as one week post-transplantation, they were mostly lost before or after engraftment, while the unmanipulated unit predominated in all of the recipients.

The present inventors have shown that culturing CD133+ cord blood cells in the presence of cytokines (SCF, TPO, IL-6 and FLT-3 ligand) and nicotinamide resulted in better and prolonged expansion of both late and early progenitors, which are important for short-term early trilineage engraftment, and reduction in the fraction of differentiated myelomonocytic cells (CD14+, CD11b+, CD11c+) and increase the fraction of less differentiated early progenitor cells, the CD34+CD38− cells. CD34+ cells obtained following culturing with NAM displayed increased migration towards SDF-1 and home to the bone marrow (24 hour post infusion) with higher efficacy than cells cultured with cytokines only or non-cultured cells. Further, in vitro studies show that these culture conditions do not support expansion of T cells and therefore only negligible amounts of cells displaying T-cell phenotype can be found in the expanded cord blood fraction (see U.S. Pat. Nos. 7,955,852 and 8,846,393, and Peled et al, 2012, Exp Hematol 40:342-55).

Horowitz et al (2014, J Clin Invest 124:3121-3128), using the double cord blood transplantation approach, demonstrated that allogeneic stem and progenitor cells ex-vivo expanded from an entire cord blood unit with cytokines and nicotinamide are capable of out-competing an unmanipulated cord blood graft, and providing rapid engraftment and robust, long term multilineage hematopoiesis.

Wagner et al (Cell Stem Cell 2016 18:144-55) reported positive results in a Phase I/II clinical trial with cord blood hematopoietic stem cells expanded with an aryl hydrocarbon receptor antagonist as a stand alone graft.

SUMMARY OF THE INVENTION

According to an aspect of some embodiments of the present invention there is provided a method of selecting a cryopreserved umbilical cord blood unit for ex-vivo expansion and transplantation into a subject, comprising:
(a) determining in the umbilical cord blood unit prior to ex-vivo expansion the following pre-cryopreservation parameters:
  (i) about $8 \times 10^6$ to about $15 \times 10^6$ total CD34+ cells;
  (ii) HLA-matched at least 4 out of 6 HLA class I (HLA-A and HLA-B, low resolution) and HLA class II (HLA-DRB1, high resolution) loci with the subject;
  (iii) about $1.8 \times 10^9$ to about $3.0 \times 10^9$ pre-cryopreserved total nucleated cells;
  (iv) about $1.5 \times 10^7$ to about $3.0 \times 10^7$ pre-cryopreserved total nucleated cells per kilogram subject weight,
(b) selecting or excluding the umbilical cord blood unit according to the parameters, thereby selecting an umbilical cord blood unit suitable for ex-vivo expansion and transplantation into the subject.

According to an aspect of some embodiments of the present invention (i) is about $8 \times 10^6$ to about $10 \times 10^6$ total CD34+ cells.

According to an aspect of some embodiments of the present invention (i) is at least $8 \times 10^6$ total CD34+ cells.

According to an aspect of some embodiments of the present invention there is provided a method of treating a hematological disease in a subject in need thereof, the method comprising:

(a) separating a single umbilical cord blood unit suitable for transplantation into the subject into (i) a first, selected blood cell fraction comprising CD133+/CD34+ selected cells and (ii) a second, unselected blood cell fraction comprising CD133/CD34 negative cells;

(b) ex vivo culturing the first blood cell fraction comprising CD133+/CD34+ selected cells under conditions allowing for cell proliferation, the conditions comprising providing nutrients, serum and a combination of cytokines including each of stem cell factor, thrombopoietin, FLt3 ligand and IL-6 and nicotinamide in an amount between 1.0 mM to 10 mM;

(c) cryopreserving the ex-vivo cultured first, CD133+/CD34+ selected blood cell fraction and the uncultured second, unselected blood cell fraction from step (b), (d) thawing the ex-vivo cultured first selected and the uncultured second, unselected blood cell fractions, and (e) transplanting the thawed ex-vivo cultured first selected and uncultured second unselected blood cell fractions from step (d) into a subject in need thereof, thereby treating the hematological disease in the subject.

According to an aspect of some embodiments of the present invention there is provided a method of treating a hematological disease in a subject in need thereof, the method consisting of:

(a) separating a single umbilical cord blood unit suitable for transplantation into the subject into (i) a first, selected blood cell fraction comprising CD133+/CD34+ selected cells and (ii) a second, unselected blood cell fraction comprising CD133/CD34 negative cells;

(b) ex vivo culturing the first blood cell fraction comprising CD133+/CD34+ selected cells under conditions allowing for cell proliferation, the conditions comprising providing nutrients, serum and a combination of cytokines including each of stem cell factor, thrombopoietin, FLt3 ligand and IL-6 and nicotinamide in an amount between 1.0 mM to 10 mM;

(c) cryopreserving the ex-vivo cultured first, selected CD133+/CD34+ blood cell fraction and the uncultured second, unselected blood cell fraction from step (b), (d) thawing the ex-vivo cultured first selected and the uncultured second, unselected blood cell fractions, and (e) transplanting the thawed ex-vivo cultured first selected and uncultured second unselected blood cell fractions from step (d) into a subject in need thereof, thereby treating the hematological disease in the subject.

According to some embodiments of the present invention the single umbilical cord blood unit suitable for transplantation is characterized by the following pre-cryopreservation parameters:

(i) at least $8 \times 10^6$ total CD34+ cells;
(ii) HLA-matched at least 4 out of 6 HLA class I (HLA-A and HLA-B, low resolution) and HLA class II (HLA-DRB1, high resolution) loci with the subject;
(iii) about $1.8 \times 10^9$ to about $3.0 \times 10^9$ pre-cryopreserved total nucleated cells, and
(iv) about $1.5 \times 10^7$ to about $3.0 \times 10^7$ pre-cryopreserved total nucleated cells per kilogram subject weight.

According to some embodiments of the present invention the cryopreserved ex-vivo cultured first selected and the uncultured second, unselected blood cell fractions are thawed on the same day of transplantation.

According to some embodiments of the present invention the cryopreserved ex-vivo cultured first selected and the uncultured second, unselected blood cell fractions are thawed and reconstituted in infusion solution.

According to some embodiments of the present invention the transplantation is affected by infusion in an infusion solution into the patient.

According to some embodiments of the present invention the infusion solution comprises 8% Human Serum Albumin (HSA) and 6.8% weight per volume Dextran 40.

According to some embodiments of the present invention the ex-vivo cultured first selected blood cell fraction is infused prior to the uncultured second, unselected blood cell fraction.

According to some embodiments of the present invention the uncultured second, unselected blood cell fraction is infused prior to the ex-vivo cultured first selected blood cell fraction.

According to some embodiments of the present invention the first ex-vivo cultured blood cell fraction comprises at least $8 \times 10^8$ total viable cells.

According to some embodiments of the present invention the second uncultured blood cell fraction comprises at least $4 \times 10^8$ total viable cells.

According to some embodiments of the present invention the hematological disease is a hematological malignancy.

According to some embodiments of the present invention the hematological malignancy is selected from the group consisting of Chronic myelogenous leukemia (CML), acute lymphoblastic leukemia (ALL), acute myelogenous leukemia (AML) and myelodysplastic syndrome (MDS).

According to some embodiments of the present invention the subject has been subjected to myeloablative therapy or other conditioning regime prior to transplantation.

According to some embodiments of the present invention the subject has been subjected to graft-versus-host disease (GvHD) prophylaxis regime prior to transplantation.

According to some embodiments of the present invention the subject is subjected to graft-versus-host disease (GvHD) prophylaxis regime following transplantation.

According to some embodiments of the present invention transplantation of the first ex vivo cultured CD133+/CD34+ blood cell fraction and the second uncultured CD133−/CD34− blood cell fraction decreases time from transplantation to neutrophil engraftment in the subject, when compared to transplantation of a single or double unit of unmanipulated cord blood.

According to some embodiments of the present invention the time to neutrophil engraftment is decreased 5-14 days when compared to transplantation of a single or double unit of unmanipulated cord blood.

According to some embodiments of the present invention the neutrophil engraftment consists of achieving an absolute neutrophil count (ANC)$\geq 0.5 \times 10^9$/L on 3 consecutive measurements on different days with subsequent donor chimerism ($\leq 10\%$ host cells by peripheral blood chimerism), on or before 42 days post transplant.

According to some embodiments of the present invention transplantation of the first ex vivo cultured CD133+/CD34+ blood cell fraction and the second uncultured CD133−/CD34− blood cell fraction decreases time from transplantation to platelet engraftment in the subject, when compared to transplantation of a single or double unit of unmanipulated cord blood.

According to some embodiments of the present invention transplantation of the first ex vivo cultured CD133+/CD34+ hematopoietic stem/progenitor blood cell fraction and the second uncultured CD133−/CD34− blood cell fraction increases the probability of platelet engraftment in the subject at 42 days post transplantation when compared to transplantation of a single or double unit of unmanipulated cord blood.

According to some embodiments of the present invention wherein transplantation of the first ex vivo cultured CD133+/CD34+ blood cell fraction and the second CD133−/CD34− uncultured blood cell fraction decreases risk of non-engraftment by day 42 after transplantation in the subject, when compared to transplantation of a single or double unit of unmanipulated cord blood.

According to some embodiments of the present invention transplantation of the first ex vivo cultured CD133+/CD34+ blood cell fraction and the second uncultured CD133−/CD34− blood cell fraction decreases the risk of non-relapse mortality after transplantation in the subject, when compared to transplantation of a single or double unit of unmanipulated cord blood.

According to some embodiments of the present invention transplantation of the first ex vivo cultured CD133+/CD34+ blood cell fraction and the second uncultured CD133−/CD34− blood cell fraction decreases the risk of non-relapse mortality at 210 days after transplantation.

According to some embodiments of the present invention transplantation of the first ex vivo cultured CD133+/CD34+ blood cell fraction and the second uncultured CD133−/CD34− blood cell fraction decreases the risk of transplantation related mortality at 1 year.

According to some embodiments of the present invention transplantation of the first ex vivo cultured CD133+/CD34+ blood cell fraction and the second uncultured CD133−/CD34− blood cell fraction decreases duration of hospitalization in the subject in the first 100 days post-transplantation, when compared to transplantation of a single or double unit of unmanipulated cord blood.

According to some embodiments of the present invention transplantation of the first ex vivo cultured CD133+/CD34+ blood cell fraction and the second uncultured CD133−/CD34− blood cell fraction decreases duration of post-transplantation hospitalization by 5-30 days.

According to some embodiments of the present invention transplantation of the first ex vivo cultured CD133+/CD34+ blood cell fraction and the second uncultured CD133−/CD34− blood cell fraction decreases risk of grade 2/3 bacterial or invasive fungal infections post-transplantation in the subject, when compared to transplantation of a single or double unit of unmanipulated cord blood.

According to some embodiments of the present invention transplantation of the first ex vivo cultured CD133+/CD34+ blood cell fraction and the second uncultured CD133−/CD34− blood cell fraction decreases risk of grade 2/3 bacterial or invasive fungal infections post-transplantation decreases risk of grade 2/3 bacterial or invasive fungal infections by 100 days post-transplantation in the subject, when compared to transplantation of a single or double unit of unmanipulated cord blood.

According to some embodiments of the present invention transplantation of the first ex vivo cultured CD133+/CD34+ blood cell fraction and the second uncultured CD133−/CD34− blood cell fraction decreases risk of acute graft-versus-host disease grade III-IV in the subject at 100 days post transplantation, when compared to transplantation of a single or double unit of unmanipulated cord blood.

According to some embodiments of the present invention transplantation of the first ex vivo cultured CD133+/CD34+ blood cell fraction and the second uncultured CD133−/CD34− blood cell fraction decreases risk of severe chronic graft-versus-host disease in the subject at 180 days post transplantation, when compared to transplantation of a single or double unit of unmanipulated cord blood.

According to some embodiments of the present invention the first and second blood cell fractions are co-administered in conjunction with an additional treatment for hematological disease.

According to some embodiments of the present invention the additional treatment is selected from the group consisting of immunosuppressive treatment, chemotherapy and radio-therapy.

According to an aspect of some embodiments of the present invention there is provided an article of manufacture comprising:

(a) a packaging material and
(b) umbilical cord blood cell fractions comprising:
(i) a first blood cell fraction suitable for transplantation into a subject in need thereof comprising CD133+/CD34+ selected cord blood cells ex-vivo cultured under conditions allowing for cell proliferation, the conditions comprising providing nutrients, serum and a combination of cytokines including each of stem cell factor, thrombopoietin, FLt3 ligand and IL-6 and nicotinamide in an amount between 1.0 mM to 10 mM; and
(ii) a second, uncultured, unselected blood cell fraction suitable for transplantation into a subject in need thereof comprising CD133/CD34 negative cells, and wherein the packaging material comprises a label or package insert indicating that the first and second umbilical cord blood cell populations are for treating a hematological disease in a subject in need thereof.

According to some embodiments of the present invention the first ex-vivo cultured blood cell fraction comprises at least $8 \times 10^8$ total viable cells.

According to some embodiments of the present invention the second uncultured blood cell fraction comprises at least $4 \times 10^8$ total viable cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DETAILED DESCRIPTION OF EMBODIMENTS OF THE INVENTION

The present invention relates to methods of selecting umbilical cord blood units for ex-vivo expansion, separation of CD133+/CD34+ positive and uncultured CD133+/CD34+ negative fractions, methods for expanding the selected CD133+/CD34+ fraction, selection of expanded populations of CD133+/CD34+ cord blood cells for transplantation to subjects in need thereof and the therapeutic use of suitable selected, ex-vivo expanded CD133+/CD34+ and unselected CD133/CD34 negative cord blood fractions for transplantation in the clinical setting, for treatment of hematological malignancies. The present invention also envisions kits comprising the expanded and unselected cord blood fractions.

The present invention also relates to a kit comprising the expanded cord blood unit, and directions for the use thereof in the treatment of hematological malignancies.

Before explaining at least one embodiment of the invention in detail, it is to be understood that the invention is not necessarily limited in its application to the details set forth in the following description. The invention is capable of other embodiments or of being practiced or carried out in various ways.

Allogeneic hematopoietic stem cell transplantation is a life-saving procedure for patients with hematologic disorders; yet wide application of this procedure is limited by the availability of suitably HLA-matched donors.

Accordingly, cord blood grafts are routinely and more successfully used in the pediatric transplantation setting (only 20% of cord blood units in banks could suffice for a 75 kg patient according to the recommended threshold cell dose). Adults receiving cord blood transplantation are at high risk of early mortality (as high as 30-60% day 100 mortality) and infection due to delayed engraftment and higher rates of engraftment failure. Indeed, publications reviewing the differences in outcomes between umbilical cord blood and other graft sources consistently report higher non-relapse mortality following cord blood transplantation, generally attributable to inadequate hematopoietic recovery, and delayed engraftment has been deemed the single greatest barrier to successful cord blood transplantation and the most important contributor to early non-relapse mortality.

A significant challenge to presently available methods for graft production is the ability to generate an expanded population of committed hematopoietic progenitor cells without compromising the numbers of less differentiated progenitor cells (CD34+CD38− or CD34+Lin− cells). The present invention provides an expansion technology utilizing nicotinamide (NAM) for increased bone marrow homing and engraftment efficacy. Engraftment is a multi-step process involving directed migration of the inoculated cells, homing to the bone marrow (BM), retention within the BM niche followed by self-renewal and differentiation. Engraftment efficacy following expansion is known to be low due to poor homing to the bone marrow compared to fresh CD34+ cells or reduced self-renewal owing to enhanced differentiation in culture.

The methods for the selection of cord blood units and ex vivo expansion of hematopoietic progenitor cells (HPC) provided herein permit increasing their numbers while maintaining their self-renewal capacity and their ability to home to the bone marrow (BM) and efficiently reconstitute hematopoiesis. Addition of nicotinamide delays differentiation and increases the homing and engraftment efficacy of cord-blood derived, purified CD133+ cells cultured with a combination of 4-cytokines (FLT3, SCF, TPO and IL6) for 21 (+/−2) days (19-23 days). As these culture conditions to not support expansion of T cells (only negligible amounts of cells displaying T-cell phenotype can be found in the cultured, expanded cells), the present invention provides an uncultured, unmanipulated fraction derived from the same cord blood unit to provide T-cells.

The present invention provides criteria for selection of cord blood units for preparation of cultured, ex-vivo expanded CD133+/CD34+ and uncultured, CD133/CD34 negative cord blood fractions, methods for the culture and ex-vivo expansion of the CD133+/CD34+ cord blood fraction, criteria for selection of expanded CD133+/CD34+ and uncultured, CD133/CD34 negative cord blood fractions suitable for transplantation with a high probability of effective engraftment and methods of cryopreservation and preparation of the cultured and uncultured cord blood fractions. The present invention also provides methods for the use of expanded CD133+/CD34+ and uncultured, CD133/CD34 negative cord blood fractions meeting the selection criteria for transplantation in the clinical setting, for treatment of malignant blood disorders.

Selection of Cord Blood Units for Ex-Vivo Expansion

According to some embodiments, the present invention provides a method of selecting a cryopreserved umbilical cord blood unit for ex-vivo expansion and transplantation into a subject, comprising: determining in said umbilical cord blood unit prior to ex-vivo expansion the following pre-cryopreservation parameters:

(i) about $8 \times 10^6$ to about $15 \times 10^6$ total CD34+ cells;
(ii) HLA-matched at least 4 out of 6 HLA class I (HLA-A and HLA-B, low resolution) and HLA class II (HLA-DRB1, high resolution) loci with said subject;
(iii) about $1.8 \times 10^9$ to about $3.0 \times 10^9$ pre-cryopreserved total nucleated cells;
(iv) about $1.5 \times 10^7$ to about $3.0 \times 10^7$ pre-cryopreserved total nucleated cells per kilogram subject weight, and selecting or excluding said umbilical cord blood unit according to said parameters, thereby selecting an umbilical cord blood unit suitable for ex-vivo expansion and transplantation into the subject.

All cord blood units are procured from public banks that meet national applicable regulations. Donors are screened and tested in accordance with the relevant regulatory requirements. Cord blood banks typically employ methods for efficient storage of freshly harvested umbilical cord blood, including red blood cell depletion and plasma depletion, resulting in volume reduction, and cryopreservation of the reduced volume cord blood unit. Prior to cryopreservation of the cord blood unit, a sample of the unit is analyzed to produce a profile of the unit, including, but not limited to, cell viability, amounts of specific cell populations, human leukocyte antigen (HLA) typing, and safety criteria such as bacterial/viral contamination, and unit volume, providing, inter alia, total values for the entire unit, relative values (e.g., percentage of any specific cell type from the total number of cells), and values adjusted for volume (e.g., concentration of any specific cell type in a unit volume). As used herein, the term "cryopreservation" refers to a process wherein biological entities subject to damage by unregulated chemical kinetics (e.g., cells, tissues, organelles) are preserved by cooling to extremely low temperatures, typically −80° C. with solid carbon dioxide or −196° C. using liquid nitrogen. In one embodiment, cord blood cells are cryopreserved with liquid nitrogen. Methods of preservation of hematopoietic cell populations are well known in the art (see, Watts et al, Cryopreservation and Freeze-Drying Protocols, in Methods in Molecular Biology, 2007; 368:237-259).

As used herein, the term "pre-cryopreservation" refers to parameters, values or characteristics recorded prior to cryopreservation, for example, prior to cryopreservation of a banked, cryopreserved cord blood unit. In some embodiments, such "pre-cryopreservation" data can be referred to for the selection of candidate cord blood units for use in the methods of the present invention.

Thus, according to an embodiment of the present invention, pre-cryopreserved parameters of total CD34+ cells, total nucleated cells, and red blood cell depletion and volume reduction are determined for an umbilical cord blood unit in order to select or exclude the cord blood unit for ex-vivo expansion and transplantation. When the identity of the candidate for transplantation (e.g., the "subject") is known, parameters such as HLA-match (compatibility) and pre-cryopreservation total nucleated cells per kilogram subject weight can also be determined and serve as a selection criteria.

In particular embodiments, cord blood units selected for ex-vivo expansion have pre-cryopreservation total CD34+ values of about $8 \times 10^6$ to about $15 \times 10^6$ total CD34+ cells, about $9 \times 10^6$ to about $13 \times 10^6$ total CD34+ cells, about $10 \times 10^6$ to about $12 \times 10^6$ total CD34+ cells. In one embodiment, cord blood units selected for ex-vivo expansion have at least $12 \times 10^6$ total pre-cryopreserved CD34+ cells. In one embodiment, cord blood units selected for ex-vivo expansion have at least $8 \times 10^6$ total pre-cryopreserved CD34+ cells. In one embodiment, cord blood units selected for ex-vivo expansion have at least $10 \times 10^6$ total pre-cryopreserved CD34+ cells.

In particular embodiments, cord blood units selected for ex-vivo expansion have pre-cryopreservation total nucleated cell values of about $1.8 \times 10^9$ to about $3.0 \times 10^9$ total nucleated cells, about $2 \times 10^9$ to about $2.7 \times 10^9$ total nucleated cells or about $2.2 \times 10^9$ to about $2.5 \times 10^9$ total nucleated cells. In one embodiment, cord blood units selected for ex-vivo expansion have at least $2.5 \times 10^9$ pre-cryopreserved total nucleated cells. In one embodiment, cord blood units selected for ex-vivo expansion have at least $2.0 \times 10^9$ pre-cryopreserved total nucleated cells. In one embodiment, cord blood units selected for ex-vivo expansion have at least $1.8 \times 10^9$ pre-cryopreserved total nucleated cells. Typically, nucleated cells can be counted manually in haemocytometers (e.g., Neubauer) or with an automated counter.

In particular embodiments, cord blood units selected for ex-vivo expansion have pre-cryopreservation total nucleated cells per kilogram subject weight of about $1.5 \times 10^7$ to about $3.0 \times 10^7$ total nucleated cells per kilogram subject weight, about $1.7 \times 10^7$ to about $2.8 \times 10^7$ total nucleated cells per kilogram subject weight, about $1.9 \times 10^7$ to about $2.5 \times 10^7$ total nucleated cells per kilogram subject weight or about $2 \times 10^7$ to about $2.2 \times 10^7$ total nucleated cells per kilogram subject weight. In one embodiment, cord blood units selected for ex-vivo expansion have at least $3.0 \times 10^7$ pre-cryopreserved total nucleated cells per kilogram subject weight. In one embodiment, cord blood units selected for ex-vivo expansion have at least $2.3 \times 10^7$ pre-cryopreserved total nucleated cells per kilogram subject weight. In one embodiment, cord blood units selected for ex-vivo expansion have at least $1.5 \times 10^7$ pre-cryopreserved total nucleated cells per kilogram subject weight.

In particular embodiments, cords blood units selected for ex-vivo expansion are pre-cryopreservation HLA-matched at least 4 out of 6 HLA class I (HLA-A and HLA-B, low resolution) and HLA class II (HLA-DRB1, high resolution) loci with said subject, at least 5 out of 6 HLA class I (HLA-A and HLA-B, low resolution) and HLA class II (HLA-DRB1, high resolution) loci with said subject, or at 6 out of 6 HLA class I (HLA-A and HLA-B, low resolution) and HLA class II (HLA-DRB1, high resolution) loci with said subject. In some embodiments, the cord units are pre-cryopreservation HLA-matched at least 4 out of 6 HLA class I (HLA-A and HLA-B, low resolution) and HLA class II (HLA-DRB1, high resolution) loci with said subject, with at least one HLA-DRB1 match. In some embodiments, the cord units are pre-cryopreservation HLA-matched at least 5 out of 6 HLA class I (HLA-A and HLA-B, low resolution) and HLA class II (HLA-DRB1, high resolution) loci with said subject. In some embodiments, the cord units are pre-cryopreservation HLA-matched at least 5 out of 6 HLA class I (HLA-A and HLA-B, low resolution) and HLA class II (HLA-DRB1, high resolution) loci with said subject, with at least one HLA-DRB1 match. Typically, Class I HLA (or Major Histocompatibility Complex, MHC) antigens are determined on the cord blood cells by a microcytotoxicity assay using alloantisera for specific HLAs, complement for cytotoxicity and a dye to identify killed cells. HLA Class II are typically determined by the mixed lymphocyte reaction (MLR), measuring lymphocyte proliferation following culture of mixed lymphocyte populations. HLA DR antigens can be identified by B cell antisera in a microcytotoxicity assay with enriched B cells. Antisera can be replaced by specific monoclonal antibodies.

In some embodiments, the cords blood units selected for ex-vivo expansion have at least $8 \times 10^6$ total pre-cryopreserved CD34+ cells and at least $1.5 \times 10^7$ pre-cryopreserved total nucleated cells per kilogram subject weight.

In some embodiments, the cords blood units selected for ex-vivo expansion have at least $10 \times 10^6$ total pre-cryopreserved CD34+ cells and at least $2.5 \times 10^7$ pre-cryopreserved total nucleated cells per kilogram subject weight.

Examples of exemplary pre-cryopreservation criteria for selection of cord blood units for ex-vivo expansion and transplantation into a subject are presented in Tables I-IV hereinbelow.

TABLE I

| CBU Pre-cryopreservation selection criteria | |
| --- | --- |
| Parameter | Value |
| Total CD34+ cells | At least $12 \times 10^6$ |
| HLA compatibility | HLA- matched at at least 4 out of 6 HLA class I (HLA-A and HLA-B, low resolution) and HLA class II (HLA-DRB1, high resolution) loci with said subject |
| Total Nucleated Cells (TNC) | At least $1.8 \times 10^9$ |
| Total Nucleated Cells per kilogram subject weight | At least $2.5 \times 10^7$ |

TABLE II

| CBU Pre-cryopreservation selection criteria | |
| --- | --- |
| Parameter | Value |
| Total CD34+ cells | At least $10 \times 10^6$ |
| HLA compatibility | HLA- matched at at least 5 out of 6 HLA class I (HLA-A and HLA-B, low resolution) and HLA class II (HLA-DRB1, high resolution) loci with said subject |
| Total Nucleated Cells (TNC) | At least $2.7 \times 10^9$ |
| Total Nucleated Cells per kilogram subject weight | At least $2.0 \times 10^7$ |

TABLE III

| CBU Pre-cryopreservation selection criteria | |
| --- | --- |
| Parameter | Value |
| Total CD34+ cells | At least $8 \times 10^6$ |
| HLA compatibility | HLA- matched at at least 4 out of 6 HLA class I (HLA-A and HLA-B, low resolution) and HLA class II (HLA-DRB1, high resolution) loci with said subject |
| Total Nucleated Cells (TNC) | At least $1.8 \times 10^9$ |
| Total Nucleated Cells per kilogram subject weight | At least $1.5 \times 10^7$ |

TABLE IV

CBU Pre-cryopreservation selection criteria

| Parameter | Value |
| --- | --- |
| Total CD34+ cells | At least 13 × 10$^6$ |
| HLA compatibility | HLA- matched at at least 4 out of 6 HLA class I (HLA-A and HLA-B, low resolution) and HLA class II (HLA-DRB1, high resolution) loci with said subject |
| Total Nucleated Cells (TNC) | At least 2.2 × 10$^9$ |
| Total Nucleated Cells per kilogram subject weight | At least 2.7 × 10$^7$ |

As used herein the term "ex-vivo" refers to a process in which cells are removed from a living organism and are propagated outside the organism (e.g., in a test tube, in a cell culture bag, etc).

As used herein, the term "in-vitro" refers to a process in which cells originating from a cell line or lines (such as embryonic cell lines, etc.) maintained in the laboratory, are manipulated outside of an organism. Such cell lines are often immortalized cells.

As used herein, the phrase "stem cells" refers both to the lineage committed earliest renewable cell population responsible for generating rapid cell mass in a tissue or body and the very early progenitor cells, which are somewhat less differentiated, not yet committed to a specific lineage and can readily revert to become a part of the long-term renewable cell population. Hematopoietic stem cells are stem cells that can regenerate the cellular components of the blood, such as erythrocytes, leukocytes, platelets, etc.

As used herein, the phrases "non-stem", "non-progenitor" and "committed cells" refer to cells at various stages of differentiation, which generally no longer retain the ability to revert to become a part of a renewable cell population. Methods of ex-vivo culturing stem, progenitor, and non-stem, non-progenitor committed cells are well known in the art of cell culturing. To this effect, see for example, the text book "Culture of Animal Cells—A Manual of Basic Technique" by Freshney, Wiley-Liss, N.Y. (1994), Third Edition, the teachings of which are hereby incorporated by reference.

Once suitable cryopreserved cord blood units have been identified, they may be transported for further processing (e.g., thawing and ex-vivo expansion), or they may be marked and maintained frozen until need arise for further processing in preparation for transplantation. Thus, a "bank" of cryopreserved cord blood units suitable for ex-vivo expansion and transplantation, and a corresponding database of the units can be established, enabling more rapid access to suitable cord blood units.

In some embodiments, cord blood units selected for ex-vivo expansion have at least 1.8×10$^9$ pre-cryopreserved total nucleated cells and at least 1.5×10$^7$ pre-cryopreserved total nucleated cells per kilogram subject weight.

In some embodiments, cord blood units selected for ex-vivo expansion have at least 2.5×10$^9$ pre-cryopreserved total nucleated cells and at least 2.0×10$^7$ pre-cryopreserved total nucleated cells per kilogram subject weight.

Further processing of cord blood units selected suitable for ex-vivo expansion and transplantation includes thawing the selected, cryopreserved unit, and determining suitability of the thawed cord blood cells for proceeding to further selection, separation of a CD133+/CD34+ cord blood cell fraction from the CD133−/CD34− cord blood cell fraction.

Thus, according to some embodiments, there is provided a method for selecting a thawed umbilical cord blood unit for ex-vivo expansion and transplantation into a subject, the method comprising determining percent viability of the cells in said thawed umbilical cord blood unit and selecting units having about 40% to about 85% viability prior to separation of said cord blood unit into CD133+/CD34+ and CD/133−/CD34− fractions, thereby selecting a thawed umbilical cord unit suitable for ex-vivo expansion and transplantation into the subject.

In some embodiments, units having about 40% to about 70% viability are selected. In some embodiments, units having about 42%, about 46%, about 48%, about 50%, about 52%, about 54%, about 56%, about 58%, about 60%, about 62%, about 64%, about 66%, about 68% to about 70% viability are selected.

It will be appreciated that the thawed umbilical cord blood units are typically cryopreserved cord blood units that have been selected suitable for further processing using the criteria and methods described herein.

According to some embodiments, the selected frozen cord blood unit is transferred to the manufacturing site in accordance with the procedures of the cord blood bank. Following confirmation that of the identity of the cord blood unit, the unit is stored at liquid nitrogen central storage until commencement of the cell selection and expansion procedure.

At the manufacturing site, the cord blood bag is carefully wiped using sterile alcohol wipes, thawed in a water bath at 37°±1 C and transferred to a production site (e.g. clean room) for further handling.

In some embodiments, thawed cord blood units are prepared for cell selection as follows: The thawed blood is transferred into a 175 ml centrifuge tube. The cryobag is washed with 10% w/v dextran-40 in saline solution and 5% w/v HSA and then added to the centrifuge tube. Two samples are removed to determine the cell viability and viable cell concentration of the cell suspension as well as the CD34+, CD133+ content of the thawed CBU. After centrifugation the supernatant is removed and the volume is brought to 100 ml by the addition of a PBS buffer containing 0.4% w/v sodium citrate and 1% v/v HSA. IV Ig is added and after incubation for 10 minutes at RT, the cell suspension is centrifuged and the pelleted cells are re-suspended.

In some embodiments, cords blood units selected for ex-vivo expansion are pre-cryopreservation HLA-matched at least 4 out of 6 HLA class I (HLA-A and HLA-B, low resolution) and HLA class II (HLA-DRB1, high resolution) loci with said subject and at least 8×10$^6$ total pre-cryopreserved CD34+ cells.

In some embodiments, cords blood units selected for ex-vivo expansion are pre-cryopreservation HLA-matched at least 4 out of 6 HLA class I (HLA-A and HLA-B, low resolution) and HLA class II (HLA-DRB1, high resolution) loci with said subject and at least 2.0×10$^7$ pre-cryopreserved total nucleated cells per kilogram subject weight.

As used herein, the term "viability" refers to the distinction between living and non-living cells. Cell viability may be judged by morphological changes or by changes in membrane permeability and/or physiological state inferred from the exclusion of certain dyes or the uptake and retention of others. Cell viability assays are well known in the art, including, but not limited to trypan blue or propidium iodide exclusion and rhodamine metabolic stain (Coder, D., Current Protocols in Cytometry, 1997, John Wiley and Sons, Inc., Unit 9.2, 9.2.1-9.2.14).

Thawed cord blood units excluded according to criteria of viability are discarded, and cannot proceed through further steps of processing for transplantable cord blood units. Thawed cord blood units meeting the criteria of viability can be assayed for the percent CD133+ and percent CD34+ cells in the thawed unit, and that data recorded for later reference.

In some embodiments, cords blood units selected for ex-vivo expansion are pre-cryopreservation HLA-matched at least 4 out of 6 HLA class I (HLA-A and HLA-B, low resolution) and HLA class II (HLA-DRB1, high resolution) loci with said subject, at least $1.5 \times 10^7$ pre-cryopreserved total nucleated cells per kilogram subject weight and at least $8 \times 10^6$ total pre-cryopreserved CD34+ cells.

Thawed cord blood units deemed suitable, by viability, for further processing for ex-vivo expansion and transplantation are then separated into two cord blood fractions by selection according to stem cell marker CD133+. The CD133+/CD34+ cell fraction of the cord blood unit represents a hematopoietic stem and progenitor cell population with potential to proliferate, differentiate and reconstitute all blood cell lineages, while the unselected, CD133−/CD34− "negative" cell fraction represents a fraction rich in mature immune cells such as B-cells, T-cells and natural killer (NK) cells.

In some embodiments, cords blood units selected for ex-vivo expansion are pre-cryopreservation HLA-matched at least 4 out of 6 HLA class I (HLA-A and HLA-B, low resolution) and HLA class II (HLA-DRB1, high resolution) loci with said subject and at least $1.8 \times 10^7$ pre-cryopreserved total nucleated cells.

Stem cells can be identified and enriched using stem cell markers such as CD34+, CD34+/CD38−, CD133+, CD34+/Lin−, and other stem cell markers known in the art. Identification and separation of the CD133+/CD34+ fraction of the thawed cord blood cells can be performed by selection using FACS, immunomagnetic separation or nucleic acid methods such as PCR, such as the methods of isolating or enriching for cord blood and adult stem cells described in Stem Cell Biology Daniel R. Marshak (Editor) Richard L. Gardner (Editor), Publisher: Cold Spring Harbor Laboratory Press, (2001) and Hematopoietic Stem Cell Transplantation. Anthony D. Ho (Editor) Richard Champlin (Editor), Publisher: Marcel Dekker (2000).

In a particular embodiment, the thawed cord blood unit selected suitable for ex-vivo expansion and transplantation is separated into a CD133+/CD34+ (positive) fraction and a CD133−/CD34− (negative) fraction using anti-CD133-conjugated immunomagnetic beads (CliniMacs, Milentyi Biotec, Germany).

In specific embodiments, separation of the CD133+ fraction is affected as follows: 1.2 ml of the Miltenyi CliniMACS CD133 reagent is added to the cord blood cell suspension and incubated for 5 minutes at room temperature. Buffer is added and the suspension centrifuged for 10 minutes at 450×g at room temperature. The supernatant is removed and the cell pellet is re-suspend in PBS buffer containing 0.4% w/v sodium citrate and 1% v/v HSA, and the cell suspension is transferred into a transfer bag. The CliniMACS system (Miltenyi Biotec, Germany) is assembled as per the manufacturer's instructions, and the selected CD133+ cells are collected into a "collection" transfer bag while the CD133− unselected, non-binding cells are collected into the negative fraction bag. The cells are transferred aseptically from the "collection" bag into a 175 ml centrifuge tube. The selected cell suspension is centrifuged at 450×g for 10 minutes at room temperature, the supernatant removed and the cells transferred into a sterile tube for safety testing. The cell pellet is re-suspended and the exact volume measured and recorded.

A sample of the cell suspension is removed and the cell viability and the viable cell concentration are measured. The total number of viable cells and the cell yield obtained from the column are calculated. The percentage of purified CD133+ and CD34+ cells is measured. The purity is defined as the percent of CD133+ cells within the selected cell population.

Once separated, the CD133+/CD34+ positive fraction can be expanded ex-vivo, but must first be screened for suitability for further processing, Thus, in some embodiments, the method for selecting a thawed umbilical cord blood unit for ex-vivo expansion and transplantation into a subject further comprises:

(a) separating said selected thawed umbilical cord blood unit suitable for ex-vivo expansion transplantation into said subject into (i) a first, selected blood cell fraction comprising CD133+/CD34+ selected cells and (ii) a second, unselected blood cell fraction comprising CD133/CD34 negative cells, and (b) determining in said first, selected CD133+/CD34+ fraction the following post-separation parameters:
  (i) about $20 \times 10^5$ to about $75 \times 10^5$ total cells;
  (ii) about 70% to about 85% viability;
  (iii) about 70% to about 85% CD133+ cells;
  (iv) about 70% to about 85% CD34+ cells;
  (v) about 0.02 to about 1% yield post CD133+/CD34+ selection
  (vi) about 15 to about 50 CFU/1000 cells, and
  (vii) less than 3 Eu/ml endotoxin, and (c) selecting or excluding said first, selected CD133+/CD34+ fraction according to said parameters, thereby selecting a CD133+/CD34+ cord blood fraction suitable for ex-vivo expansion and transplantation into said subject.

In particular embodiments, the CD133+/CD34+ cord blood fraction selected for ex-vivo expansion has total post-separation cell count of about $20 \times 10^5$ to about $75 \times 10^5$ cells, about $25 \times 10^5$ to about $65 \times 10^5$ cells, about $30 \times 10^5$ to about $60 \times 10^5$ cells, about $36 \times 10^5$ to about $55 \times 10^5$ cells and about $40 \times 10^5$ to about $50 \times 10^5$ cells. In one embodiment, the CD133+/CD34+ cord blood fraction selected for ex-vivo expansion has a total post-separation cell count of at least $20 \times 10^6$, at least $30 \times 10^6$, at least $35 \times 10^6$, at least $40 \times 10^6$, at least $45 \times 10^6$, at least $50 \times 10^6$, at least $55 \times 10^6$, at least $60 \times 10^6$ and at least $70 \times 10^6$ total cells. In a further embodiment, the CD133+/CD34+ cord blood fraction selected for ex-vivo expansion has a total post-separation cell count of at least $25 \times 10^6$ total cells. In a further embodiment, the CD133+/CD34+ cord blood fraction selected for ex-vivo expansion has a total post-separation cell count of at least $20 \times 10^6$ total cells. In a further embodiment, the CD133+/CD34+ cord blood fraction selected for ex-vivo expansion has a total post-separation cell count of at least $45 \times 10^6$ total cells.

In some embodiments, cords blood units selected for ex-vivo expansion are pre-cryopreservation HLA-matched at least 4 out of 6 HLA class I (HLA-A and HLA-B, low resolution) and HLA class II (HLA-DRB1, high resolution) loci with said subject and have at least $1.8 \times 10^9$ pre-cryopreserved total nucleated cells.

In some embodiments, cords blood units selected for ex-vivo expansion are pre-cryopreservation HLA-matched at least 4 out of 6 HLA class I (HLA-A and HLA-B, low resolution) and HLA class II (HLA-DRB1, high resolution) loci with said subject and have at least $2.5 \times 10^9$ pre-cryopreserved total nucleated cells.

In some embodiments, CD133+/CD34+ cord blood fractions having about 70% to about 85% viability are selected. In some embodiments, CD133+/CD34+ cord blood fractions having about 71%, about 73%, about 75%, about 78%, about 80%, about 82%, about 83%, about 84% to about 85% viability are selected. In a further embodiment, the CD133+/CD34+ cord blood fraction selected for ex-vivo expansion has at least 70% viable cells. In a further embodiment, the CD133+/CD34+ cord blood fraction selected for ex-vivo expansion has at least 77% viable cells. In a further embodiment, the CD133+/CD34+ cord blood fraction selected for ex-vivo expansion has at least 85% viable cells.

The CD133+, CD34+ and CD133+/CD34+ cell content of the separated cord blood fraction is critical to the successful engraftment of the transplanted expanded cord blood cells, and is thus a central criterion for proceeding to ex-vivo expansion. Thus, in particular embodiments, the CD133+/CD34+ cord blood fraction selected for ex-vivo expansion has total post-separation cell count of about 70% to about 85% CD133+ cells, about 73% to about 82% CD133+ cells, about 75% to 80% CD133+ cells and about 76-79% CD133+ cells. In one embodiment, the CD133+/CD34+ cord blood fraction selected for ex-vivo expansion has a total post-separation CD133+ cell count of at least 70%, at least 74%, at least 78%, at least 80%, at least 83% or at least 85% CD133+ cells. In a further embodiment, the CD133+/CD34+ cord blood fraction selected for ex-vivo expansion has a total post-separation CD133+ cell count of at least 80% CD133+ cells post-separation for CD133+. In a further embodiment, the CD133+/CD34+ cord blood fraction selected for ex-vivo expansion has a total post-separation CD133+ cell count of at least 70% CD133+ cells post-separation for CD133+. In a further embodiment, the CD133+/CD34+ cord blood fraction selected for ex-vivo expansion has a total post-separation CD133+ cell count of at least 75% CD133+ cells post-separation for CD133+.

Thus, in particular embodiments, the CD133+/CD34+ cord blood fraction selected for ex-vivo expansion has total post-separation cell count of about 70% to about 85% CD133+ cells, about 73% to about 82% CD133+ cells, about 75% to 80% CD133+ cells and about 76-79% CD34+ cells. In one embodiment, the CD133+/CD34+ cord blood fraction selected for ex-vivo expansion has a total post-separation CD34+ cell count of at least 70%, at least 74%, at least 78%, at least 80%, at least 83% or at least 85% CD34+ cells. In a further embodiment, the CD133+/CD34+ cord blood fraction selected for ex-vivo expansion has a total post-separation CD34+ cell count of at least 82% CD34+ cells post-separation for CD133+. In a further embodiment, the CD133+/CD34+ cord blood fraction selected for ex-vivo expansion has a total post-separation CD34+ cell count of at least 70% CD133+ cells post-separation for CD133+. In a further embodiment, the CD133+/CD34+ cord blood fraction selected for ex-vivo expansion has a total post-separation CD34+ cell count of at least 78% CD133+ cells post-separation for CD133+.

In particular embodiments, the post-selection yield of the CD133+/CD34+ cord blood fraction selected for ex-vivo expansion is about 0.02% to about 1.0%, about 0.05% to about 0.8%, about 0.08% to about 0.7%, about 0.1% to about 0.55%, about 0.25% to about 0.45% and about 0.3-0.4% following separation for CD133+. In one embodiment, the post-selection yield of the CD133+/CD34+ cord blood fraction selected for ex-vivo expansion is at least 0.01%, at least 0.05%, at least 0.1%, at least 0.3%, at least 0.5%, at least 0.65%, at least 0.75%, at least 0.9% or at least 1.0% post-selection for CD133+. In a further embodiment, the post-selection yield of the CD133+/CD34+ cord blood fraction selected for ex-vivo expansion is at least 0.02% post-separation. In a further embodiment, the post-selection yield of the CD133+/CD34+ cord blood fraction selected for ex-vivo expansion is at least 0.3% post-separation. In a further embodiment, the post-selection yield of the CD133+/CD34+ cord blood fraction selected for ex-vivo expansion is at least 0.5% post-separation. In a further embodiment, the post-selection yield of the CD133+/CD34+ cord blood fraction selected for ex-vivo expansion is at least 0.8% post-separation.

In some embodiments, the CD133+/CD34+ cord blood fraction selected for ex-vivo expansion has about 15 to about 75 CFU per 1000 cells, about 20 to about 60 CFU per 1000 cells, about 25 to about 50 CFU per 1000 cells, about 30 to about 40 CFU per 1000 cells post-separation. In one embodiment, the CD133+/CD34+ cord blood fraction selected for ex-vivo expansion has at least 15 CFU per 1000 cells, at least 22 CFU per 1000 cells, at least 25 CFU per 1000 cells, at least 30 CFU per 1000 cells, at least 36 CFU per 1000 cells, at least 40 CFU per 1000 cells, at least 45 CFU per 1000 cells, at least 52 CFU per 1000 cells, at least 60 CFU per 1000 cells, at least 68 CFU per 1000 cells or at least 75 CFU per 1000 cells post-selection for CD133+. In a further embodiment, the CD133+/CD34+ cord blood fraction selected for ex-vivo expansion has at least 15 CFU per 1000 cells following selection for CD133+. In a further embodiment, the CD133+/CD34+ cord blood fraction selected for ex-vivo expansion has at least 25 CFU per 1000 cells following selection for CD133+. In a further embodiment, the CD133+/CD34+ cord blood fraction selected for ex-vivo expansion has at least 40 CFU per 1000 cells following selection for CD133+. In a further embodiment, the CD133+/CD34+ cord blood fraction selected for ex-vivo expansion has at least 45 CFU per 1000 cells following selection for CD133+.

Examples of exemplary criteria for selection of thawed cord blood units suitable for ex-vivo expansion and transplantation into a subject are presented in Tables V-VIII hereinbelow.

TABLE V

Cord Blood Selection criteria for Expansion

| Parameter | Value |
| --- | --- |
| Total cells | At least $35 \times 10^5$ |
| Viability | At least 85% |
| CD133+ cell fraction | At least 77% |
| CD34+ cell fraction | At least 83% |
| CFU per 1000 cells | At least 23 |
| Yield post-selection | At least 0.5% |
| Endotoxin | No more than 3 Eu/ml |

TABLE VI

Cord Blood Selection criteria for Expansion

| Parameter | Value |
| --- | --- |
| Total cells | At least $20 \times 10^5$ |
| Viability | At least 70% |
| CD133+ cell fraction | At least 70% |
| CD34+ cell fraction | At least 70% |
| CFU per 1000 cells | At least 15 |
| Yield post-selection | At least 0.02% |
| Endotoxin | No more than 3 Eu/ml |

TABLE VII

Cord Blood Selection criteria for Expansion

| Parameter | Value |
| --- | --- |
| Total cells | At least 45 × $10^5$ |
| Viability | At least 85% |
| CD133+ cell fraction | At least 72% |
| CD34+ cell fraction | At least 83% |
| CFU per 1000 cells | At least 18 |
| Yield post-selection | At least 0.5% |
| Endotoxin | No more than 3 Eu/ml |

TABLE VIII

Cord Blood Selection criteria for Expansion

| Parameter | Value |
| --- | --- |
| Total cells | At least 55 × $10^5$ |
| Viability | At least 76% |
| CD133+ cell fraction | At least 85% |
| CD34+ cell fraction | At least 76% |
| CFU per 1000 cells | At least 35 |
| Yield post-selection | At least 0.09% |
| Endotoxin | No more than 3 Eu/ml |

Sterility and safety of the thawed, CD133+/CD34+ cord blood unit for ex-vivo expansion and transplantation is assured by monitoring, inter alia, the endotoxin content and presence of bacterial, fungal, viral and mycoplasma contamination. In some embodiments, the CD133+/CD34+ cord blood fraction selected for ex-vivo expansion has an endotoxin content of no more than 3 Eu/ml at any time during the expansion (cell culturing) process. In some embodiments, the CD133+/CD34+ cord blood fraction selected for ex-vivo expansion is free of bacterial, yeast, mold and mycoplasm following selection for CD133+ and on any day tested. In some embodiments, endotoxin content is monitored on days 0 and 7 of the ex-vivo expansion. In some embodiments, bacteria, yeast, mold and mycoplasma are monitored on days 0, 7 and 14 of the ex-vivo expansion.

In some embodiments, the CD133+/CD34+ cord blood fraction selected for ex-vivo expansion has at least 15 CFU per 1000 cells and a post-selection yield of at least 0.02%. In other embodiments, the CD133+/CD34+ cord blood fraction selected for ex-vivo expansion has at least 15 CFU per 1000 cells, a post-selection yield of at least 0.02% and a total post-separation CD133+ cell count of at least 75% CD133+ cells post-separation for CD133+. In other embodiments, the CD133+/CD34+ cord blood fraction selected for ex-vivo expansion has at least 35 CFU per 1000 cells and a post-selection yield of at least 0.1%.

In other embodiments, the CD133+/CD34+ cord blood fraction selected for ex-vivo expansion has at least 15 CFU per 1000 cells and a total post-separation CD133+ cell count of at least 70% CD133+ cells post-separation for CD133+.

The unselected negative, CD133− fraction comprises the repertory of immune cells, including, but not limited to T lymphocytes, B lymphocytes and Natural Killer (NK) cells. Following selection of the thawed cord blood cells for CD133+ cells, unselected negative, CD133− fraction is prepared for cryopreservation by washing and suspension in cryopreservation solution. Many cryopreservation solutions are commercially available. In some embodiments, the cryopreservation solution is CryoStor® CS10 (BioLife Solutions, Inc). Prior to cryopreservation, the unselected, CD133/CD34 negative cord blood cell fraction is also monitored for parameters including viability, CD3+ cell (T-cell) content, CD133+/CD34+ content and sterility. Thus, in some embodiments, the present invention provides a method of selecting unselected umbilical cord blood cell fractions comprising CD133/CD34 negative cells for transplantation into a subject, comprising:

(a) determining in said uncultured umbilical cord blood fraction following selection for CD133/CD34 negative cells the following parameters:
   (i) about $4\times10^8$ to about $15\times10^8$ total viable cells;
   (ii) about 70-85% viability of the cells;
   (iii) about $2.4\times10^7$ to about $8\times10^7$ CD3+ cells;
   (iv) no bacterial, yeast or mold growth, and (b) selecting or excluding said unselected umbilical cord blood cell fraction according to said parameters, thereby selecting an unselected umbilical cord blood cell fraction comprising CD133/CD34 negative cells suitable for transplantation into the subject.

In some embodiments, the CD133+/CD34+ cord blood fraction selected for ex-vivo expansion has a total post-separation cell count of at least $20\times10^6$ total cells and at least 70% viable post-separation cells.

In some embodiments, the CD133+/CD34+ cord blood fraction selected for ex-vivo expansion has a total post-separation cell count of at least $20\times10^6$ total cells, and at least 80% CD133+ cells.

In other embodiments, the CD133+/CD34+ cord blood fraction selected for ex-vivo expansion has at least 15 CFU per 1000 cells, a post-selection yield of at least 0.02% and a total post-separation CD34+ cell count of at least 70% CD34+ cells post-separation for CD133+.

In some embodiments, unselected CD133/CD34 negative cord blood fractions having about 70% to about 85% viability are selected for transplantation. In some embodiments, the CD133/CD34 negative cord blood fractions having about 71%, about 73%, about 75%, about 78%, about 80%, about 82%, about 83%, about 84% to about 85% viability are selected. In a further embodiment, the CD133/CD34 negative cord blood fraction selected for transplantation has at least 70% viable cells.

In some embodiments, the CD133+/CD34+ cord blood fraction selected for ex-vivo expansion has a total post-separation cell count of at least $20\times10^6$ total cells, and at least 70% CD133+ cells.

In some embodiments, the CD133+/CD34+ cord blood fraction selected for ex-vivo expansion has a total post-separation cell count of at least $20\times10^6$ total cells, and at least 70% CD34+ cells.

In other embodiments, the CD133+/CD34+ cord blood fraction selected for ex-vivo expansion has at least 15 CFU per 1000 cells, a post-selection yield of at least 0.02% and a total post-separation CD34+ cell count of at least 85% CD133+ cells post-separation for CD133+.

In other embodiments, the CD133+/CD34+ cord blood fraction selected for ex-vivo expansion has at least 15 CFU per 1000 cells, a post-selection yield of at least 0.02% and a total post-separation CD133+ cell count of at least 70% CD133+ cells post-separation for CD133+.

In some embodiments, the CD133+/CD34+ cord blood fraction selected for ex-vivo expansion has at least 70% viability and at least 70% CD34+ cells. In some embodiments, unselected CD133/CD34 negative cord blood fractions having about $4\times10^8$ to about $15\times10^8$ total viable cells are selected for transplantation. In some embodiments, the number of total viable cells in the CD133/CD34 negative fraction selected for transplantation is about $6\times10^8$ to about $13\times10^8$ cells, about $7.5\times10^8$ to about $11\times10^8$ viable cells or about $9\times10^8$ to about $10\times10^8$ viable cells. In some embodiments, the number of total viable cells in the CD133/CD34 negative fraction selected for transplantation is at least $4\times10^8$, at least $6\times10^8$, at least $7.5\times10^8$, at least $9\times10^8$, at least $10\times10^8$, at least $12\times10^8$, at least $14\times10^8$ or at least $15\times10^8$ total viable cells. In a particular embodiment, the number of total viable cells in the CD133/CD34 negative fraction selected for transplantation is at least $4\times10^8$ total viable cells.

In some embodiments, the CD133+/CD34+ cord blood fraction selected for ex-vivo expansion has at least 70% viable cells and a post-selection yield of at least 0.02% CD133+/CD34+ cells. In some embodiments, the CD133+/CD34+ cord blood fraction selected for ex-vivo expansion has at least 80% CD34+ cells, 85% viable cells and a post-selection yield of at least 0.1% CD133+/CD34+ cells. In some embodiments, the CD133+/CD34+ cord blood fraction selected for ex-vivo expansion has at least 70% CD34+ cells, 80% viable cells and a post-selection yield of at least 0.02% CD133+/CD34+ cells.

In some embodiments, unselected CD133/CD34 negative cord blood fractions having about $2.4\times10^7$ to about $8\times10^7$ CD3+ cells are selected for transplantation. In some embodiments, unselected CD133/CD34 negative cord blood fractions having about $2.4\times10^7$ to about $8\times10^7$ CD3+ cells, about $3.5\times10^7$ to about $7\times10^7$ CD3+ cells, about $4.3\times10^7$ to about $6.2\times10^7$ CD3+ cells or about $4.8\times10^7$ to about $5\times10^7$ CD3+ cells are selected for transplantation. In other embodiments, unselected CD133/CD34 negative cord blood fractions having at least $2.4\times10^7$ CD3+ cells, at least $3.0\times10^7$ CD3+ cells, at least $3.5\times10^7$ CD3+ cells, at least $4.0\times10^7$ CD3+ cells, at least $4.5\times10^7$ CD3+ cells, at least $5\times10^7$ CD3+ cells, at least $6\times10^7$ CD3+ cells, at least $7\times10^7$ CD3+ cells or at least $8\times10^7$ CD3+ cells are selected for transplantation. In some embodiments, the unselected CD133/CD34 negative cord blood fractions selected for transplantation have at least $3.0\times10^7$ CD3+ cells. In some embodiments, the unselected CD133/CD34 negative cord blood fractions selected for transplantation have at least $2.4\times10^7$ CD3+ cells. In some embodiments, the unselected CD133/CD34 negative cord blood fractions selected for transplantation have at least $5\times10^7$ CD3+ cells.

In other embodiments, unselected CD133/CD34 negative cord blood fractions having at least $5\times10^7$ CD3+ cells and $6\times10^8$ total viable cells are selected for transplantation. In some embodiments, unselected CD133/CD34 negative cord blood fractions having at least $2.4\times10^7$ CD3+ cells and $4\times10^8$ total viable cells are selected for transplantation. In still other embodiments, unselected CD133/CD34 negative cord blood fractions having at least $6\times10^7$ CD3+ cells and $4\times10^8$ total viable cells are selected for transplantation.

In some embodiments, unselected CD133/CD34 negative cord blood fractions having about 0.01% to about 0.5% CD133+/CD34+ cells are selected for transplantation. In some embodiments, the CD133/CD34 negative cord blood fractions having no more than about 0.03%, about 0.05%, about 0.08%, about 0.1%, about 0.25%, about 3%, about 4% or about 5% CD133+/CD34+ cells are selected. In a further embodiment, the CD133/CD34 negative cord blood fraction selected for transplantation has no greater than 0.01% CD133+/CD34+ cells. In a further embodiment, the CD133/CD34 negative cord blood fraction selected for transplantation has no greater than 0.05% CD133+/CD34+ cells. In a further embodiment, the CD133/CD34 negative cord blood fraction selected for transplantation has no greater than 0.1% CD133+/CD34+ cells. In a further embodiment, the CD133/CD34 negative cord blood fraction selected for transplantation has no greater than 0.25% CD133+/CD34+ cells. In a further embodiment, the CD133/CD34 negative cord blood fraction selected for transplantation has no greater than 0.5% CD133+/CD34+ cells.

In some embodiments, unselected CD133/CD34 negative cord blood fractions having at least $4\times10^8$ total viable cells and 85% viability are selected for transplantation. In some embodiments, unselected CD133/CD34 negative cord blood fractions having at least 70% viability and $2.4\times10^7$ CD3+ cells are selected for transplantation.

Cryopreserved CD133/CD34 negative cord blood fractions selected suitable for transplantation can be stored and maintained frozen until needed for transplantation. In some embodiments, the CD133/CD34 negative cord blood fractions selected suitable for transplantation are stored in liquid nitrogen.

In some embodiments, unselected CD133/CD34 negative cord blood fractions having at least $4\times10^8$ total viable cells and 70% viability are selected for transplantation. In some embodiments, unselected CD133/CD34 negative cord blood fractions having at least 70% viability and $2.4\times10^7$ CD3+ cells are selected for transplantation. In some embodiments, unselected CD133/CD34 negative cord blood fractions having at least $4\times10^8$ total viable cells, at least $2.4\times10^7$ CD3+ cells and 70% viability are selected for transplantation. In some embodiments, unselected CD133/CD34 negative cord blood fractions having at least $6\times10^8$ total viable cells, at least $2.7\times10^7$ CD3+ cells and at least 75% viability are selected for transplantation. In some embodiments, unselected CD133/CD34 negative cord blood fractions having at least $4\times10^8$ total viable cells and at least 80% viability are selected for transplantation.

Separation and handling of the unselected CD133/CD34 negative cord blood fractions can comprise monitoring the cultured units for safety and contamination. Thus, according to specific embodiments, cord blood fractions or units having greater than 3.0 Eu/ml endotoxin, and/or bacterial, yeast or mold growth are excluded from cryopreservation or, if detected at any point during the preparation process, further processing is terminated and the contaminated units discarded.

Culture (Ex-Vivo Expansion) of CD133+/CD34+ Selected Fractions

Any of the methods for selection of cord blood units for ex-vivo expansion described hereinabove and each of their embodiments taken alone or in various combinations may be used for affecting the methods for culturing (Ex-vivo expansion) of CD133+/CD34+ selected fractions as is described in this section and the sections that follow.

Nicotinamide (NAM) is a water-soluble derivative of vitamin B, whose physiological active forms are nicotinamide adenine dinucleotide (NAD+/NADH) and nicotinamide adenine dinucleotide phosphate (NADP+/NADPH). The physiological active forms of NAM serve as coenzyme in a variety of important metabolic reactions. Nicotinamide is further known to inhibit the enzymatic activity of CD38, to thereby affect the cADPR signal transduction pathway.

The methods for ex-vivo expanding the CD133+CD34+ fraction selected suitable for expansion and transplantation of the present invention can be performed by providing the cells either with nicotinamide itself, or with a nicotinamide analog, a nicotinamide or a nicotinamide analog derivative or a nicotinamide or a nicotinamide analog metabolite.

As used herein, the phrase "nicotinamide analog" refers to any molecule that is known to act similarly to nicotinamide. Representative examples of nicotinamide analogs include, without limitation, benzamide, nicotinethioamide (the thiol analog of nicotinamide), nicotinic acid and α-amino-3-indolepropionic acid. The phrase "a nicotinamide or a nicotinamide analog derivative" refers to any structural derivative of nicotinamide itself or of an analog of nicotinamide. Examples of such derivatives include, without limitation, substituted benzamides, substituted nicotinamides and nicotinethioamides and N-substituted nicotinamides and nicotinthioamides. The phrase "a nicotinamide or a nicotinamide analog metabolite" refers to products that are derived from nicotinamide or from analogs thereof such as, for example, NAD, NADH and NADPH. In particular embodiments, the CD133+CD34+ fraction selected suitable for expansion and transplantation is cultured with nicotinamide for ex-vivo expansion.

Final concentrations of the nicotinamide or of the analogs, derivatives or metabolites thereof are preferably, depending on the specific application, in the millimolar ranges. For example, within about 1 mM to about 10 mM, within about 2.5 mM to about 8 mM or within about 2.5 mM to about 5 mM.

According to further features in preferred embodiments of the invention described herein, conditions for ex vivo cell proliferation comprises providing the cells with serum, nutrients and cytokines.

The cytokines can be early acting cytokines. In some embodiments, the early acting cytokines are selected from the group comprising stem cell factor, FLT3 ligand, interleukin-1, interleukin-2, interleukin-3, interleukin-6, interleukin-10, interleukin-12, tumor necrosis factor-α and thrombopoietin. In specific embodiments, the cytokines are a combination of cytokines including each of stem cell factor, thrombopoietin, FLt3 ligand, and IL-6.

According to the methods of the present invention, the CD133+CD34+ cord blood fraction selected suitable for expansion and transplantation is ex-vivo expanded by culturing the first, selected blood cell fraction comprising CD133+CD34+ selected cells ex vivo under conditions allowing for cell proliferation, said conditions which comprise providing nutrients, serum and a combination of cytokines including each of stem cell factor, thrombopoietin, FLt3 ligand, and IL-6 and, in the same culture medium, nicotinamide in an amount between 1.0 to 10.0 mM.

Thus, according the present invention, there is provided a method for preparing an umbilical cord blood unit for transplantation into a subject, the method comprising:

(a) separating a single, thawed umbilical cord blood unit suitable for transplantation into said subject into (i) a first, selected blood cell fraction comprising CD133+/CD34+ selected cells and (ii) a second, unselected blood cell fraction comprising CD133/CD34 negative cells; and (b) ex vivo culturing said first blood cell fraction comprising CD133+/CD34+ selected cells under conditions allowing for cell proliferation, said conditions comprising providing nutrients, serum and cytokines including each of stem cell factor, thrombopoietin, FLt3 ligand and IL-6 and nicotinamide in an amount between 1.0 mM to 10 mM.

In some embodiments, the single umbilical cord blood unit suitable for transplantation into a subject is a thawed cord blood unit selected suitable for ex-vivo expansion and transplantation into a subject according to the methods described herein for selecting cryopreserved umbilical cord blood for expansion and transplantation into a subject. For example, thawed single umbilical cord blood units suitable for transplantation into a subject can be characterized by (i) about $8 \times 10^6$ to about $15 \times 10^6$ total CD34+ cells, (ii) HLA-matched at least 4 out of 6 HLA class I (HLA-A and HLA-B, low resolution) and HLA class II (HLA-DRB1, high resolution) loci with said subject, (iii) about $1.8 \times 10^9$ to about $3.0 \times 10^9$ pre-cryopreserved total nucleated cells and (iv) about $1.5 \times 10^7$ to about $3.0 \times 10^7$ pre-cryopreserved total nucleated cells per kilogram subject weight.

In some embodiments, the first, selected CD133+/CD34+ blood cell fraction (a)(i) is a CD133+/CD34+ cord blood fraction selected suitable for ex-vivo expansion and transplantation into said subject according to the methods described herein for selecting a CD133+/CD34+ cord blood fraction suitable for ex-vivo expansion and transplantation into a subject. For example, the CD133+/CD34+ cord blood fraction suitable for ex-vivo expansion and transplantation into a subject can be characterized by (i) about $8 \times 10^6$ to about $15 \times 10^6$ total CD34+ cells; (ii) HLA-matching at least 4 out of 6 HLA class I (HLA-A and HLA-B, low resolution) and HLA class II (HLA-DRB1, high resolution) loci with said subject; (iii) about $1.8 \times 10^9$ to about $3.0 \times 10^9$ pre-cryopreserved total nucleated cells; and (iv) about $1.5 \times 10^7$ to about $3.0 \times 10^7$ pre-cryopreserved total nucleated cells per kilogram subject weight.

In further embodiments of the method of the present invention, cord blood fractions or units having greater than 3.0 Eu/ml endotoxin, and/or bacterial, yeast or mold growth at day 0, day 7 or at day 14 of said ex-vivo expansion are excluded from culturing (ex-vivo expansion).

In further embodiments, the serum in the culture medium for expansion of the CD133+/CD34+ cord blood fraction suitable for ex-vivo expansion and transplantation into a subject comprises 10% FBS and 50 ng each of stem cell factor, thrombopoietin, FLt3 ligand and IL-6. In specific embodiments, the culture medium for expansion of the CD133+/CD34+ cord blood fraction comprises nicotinamide at 2.5 mM. In further embodiments, culturing the cells under conditions allowing for cell proliferation comprises providing nutrients, 10% fetal bovine serum (FBS), and cytokines including 50 ng each of stem cell factor, thrombopoietin, FLt3 ligand and IL-6 and nicotinamide at 2.5 mM. In some embodiments, the nicotinamide is provided at 5.0 mM.

In some embodiments, the CD133+/CD34+ cord blood fraction suitable for ex-vivo expansion and transplantation into a subject is cultured for ex-vivo expansion by culturing under the conditions described herein for 18-25 days. In specific embodiments, the CD133+/CD34+ cord blood fraction is cultured for 18, for 19, for 20, for 21, for 22, for 23, 24 or for 25 days. In some embodiments, the CD133+/CD34+ cord blood fraction is cultured for ex-vivo expansion for 21 days.

As mentioned herein, culturing the CD133+/CD34+ cord blood fraction for ex-vivo expansion can comprise monitoring the cultured units for safety and contamination. Thus, according to specific embodiments, cord blood fractions or units having greater than 3.0 Eu/ml endotoxin, and/or bacterial, yeast or mold growth at day 7 or at day 14 of said ex-vivo expansion are excluded from culturing (ex-vivo expansion) or, if detected during the culturing process, culturing (expansion) is terminated and the contaminated units discarded.

Selection of Ex-Vivo Expanded Cord Blood Units for Transplantation

At completion of the culturing (ex-vivo expansion) of the CD133+/CD34+ cord blood fraction selected suitable for ex-vivo expansion, the ex-vivo cultured first selected CD133+/CD34+ can be harvested for storage.

Any of the methods for selection of cord blood units for ex-vivo expansion described hereinabove, and for expansion (ex-vivo culturing) of cord blood units described hereinabove, and each of their embodiments taken alone or in various combinations may be used for affecting the methods for selecting cultured (ex-vivo expanded) CD133+/CD34+ selected fractions as is described in this section and the sections that follow.

Prior to storage, the ex-vivo expanded CD133+CD34+ cord blood fraction is characterized for suitability for cryopreservation as an expanded CD133+CD34+ cord blood fraction for transplantation into a subject. Thus, according to the present invention, there is provided a method of selecting ex-vivo cultured umbilical cord blood cell fractions comprising CD133+CD34+ selected cord blood cells for transplantation into a subject, the method comprising (a) determining in said ex-vivo cultured umbilical cord blood fraction following ex-vivo expansion the following parameters:

(i) about $8 \times 10^8$ to about $15 \times 10^8$ total viable cells;
(ii) about 70%-85% viability of the cells;
(iii) about 7-15% CD34+ cells;
(iv) about $5.6 \times 10^7$ to about $5 \times 10^8$ total CD34+ cells;
(v) about $2.4 \times 10^7$ to about $2 \times 10^8$ total CD133+ cells;
(vi) about $8 \times 10^5$ to about $25 \times 10^5$ CD133+/CD38− cells;
(vii) about $8 \times 10^7$ to about $15 \times 10^9$ total CD14+ cells,
(viii) about $2 \times 10^8$ to about $2 \times 10^9$ total CD15+ cells,
(ix) about $8 \times 10^7$ to about $8 \times 10^9$ total CD11b+ cells,
(x) about $3.2 \times 10^7$ to about $3 \times 10^8$ total CD1(a+c)+ cells,
(xi) No cultured mycoplasma or bacterial, yeast or mold growth, and
(b) selecting or excluding said ex-vivo cultured umbilical cord blood fraction according to said parameters, thereby selecting an ex-vivo cultured CD133+/CD34+ umbilical cord blood fraction suitable for transplantation into the subject.

In some embodiments, ex-vivo expanded CD133+/CD34+ cord blood fractions having total of about $8 \times 10^8$ to about $15 \times 10^8$ total viable cells are selected. In some embodiments, ex-vivo expanded CD133+/CD34+ cord blood fractions having total of about $9 \times 10^8$ to about $13 \times 10^8$ total viable cells, about $10 \times 10^8$ to about $12 \times 10^8$ or about $10.5 \times 10^8$ to about $11 \times 10^8$ total viable cells are selected for transplantation. In one embodiment, the ex-vivo expanded CD133+/CD34+ cord blood fraction selected for transplantation has at least $8 \times 10^8$, at least $10 \times 10^8$, at least $11 \times 10^8$, at least $12 \times 10^8$, at least $13 \times 10^8$, at least $14 \times 10^8$ and at least $15 \times 10^8$ total viable cells. In a particular embodiment, the ex-vivo expanded CD133+/CD34+ cord blood fraction selected for transplantation has at least $8 \times 10^8$ total viable cells. In a particular embodiment, the ex-vivo expanded CD133+/CD34+ cord blood fraction selected for transplantation has at least $11.5 \times 10^8$ total viable cells. In a particular embodiment, the ex-vivo expanded CD133+/CD34+ cord blood fraction selected for transplantation has at least $15 \times 10^8$ total viable cells.

In some embodiments, ex-vivo expanded CD133+/CD34+ cord blood fractions having about 70% to about 85% viability are selected. In some embodiments, ex-vivo expanded CD133+/CD34+ cord blood fractions having about 71%, about 73%, about 75%, about 78%, about 80%, about 82%, about 83%, about 84% to about 85% viability are selected for transplantation. In some embodiments, ex-vivo expanded CD133+/CD34+ cord blood fractions having at least 71%, at least 73%, at least 75%, at least 78%, at least 80%, at least 82%, at least 83%, at least 84% or at least 85% viability are selected. In a further embodiment, the ex-vivo expanded CD133+/CD34+ cord blood fraction selected for transplantation has at least 70% viable cells. In a further embodiment, the ex-vivo expanded CD133+/CD34+ cord blood fraction selected for transplantation has at least 78% viable cells. In a further embodiment, the ex-vivo expanded CD133+/CD34+ cord blood fraction selected for transplantation has at least 83% viable cells.

The CD133+, CD34+ and CD133+/CD34+, CD133+/CD38−, CD14+, CD15+, CD11b+ and CD1(a and c)+ cell content of the ex-vivo expanded CD133+/CD34+ cord blood fraction is critical to the successful engraftment of the transplanted expanded cord blood cells, and is thus a central criterion for selecting proceeding to ex-vivo expansion.

Thus, in a particular embodiment, an ex-vivo expanded CD133+/CD34+ cord blood fraction selected for transplantation has a total post-expansion (post-culturing) portion of CD34+ cells of at least 7%, at least 8%, at least 9%, at least 10%, at least 11%, at least 12%, at least 13%, at least 14% or at least 15% CD34+ cells. In a further embodiment, the CD133+/CD34+ cord blood fraction selected for transplantation has a total post-expansion (post-culturing) portion of CD34+ cells of at least 7%. In a further embodiment, the CD133+/CD34+ cord blood fraction selected for transplantation has a total post-expansion (post-culturing) portion of CD34+ cells of at least 7.8%. In a further embodiment, the CD133+/CD34+ cord blood fraction selected for transplantation has a total post-expansion (post-culturing) portion of CD34+ cells of at least 9%. In a further embodiment, the CD133+/CD34+ cord blood fraction selected for transplantation has a total post-expansion (post-culturing) portion of CD34+ cells of at least 13%.

Thus, in particular embodiments, the ex-vivo expanded CD133+/CD34+ cord blood fraction selected for transplantation has total post-expansion (post-culturing) CD34+ cell count of about $5.6 \times 10^7$ to about $5 \times 10^8$ CD34+ cells. In some embodiments, the ex-vivo expanded CD133+/CD34+ cord blood fraction selected for transplantation has total post-expansion (post-culturing) CD34+ cell count of about $6 \times 10^7$ to about $4 \times 10^8$, about $9 \times 10^7$ to about $3 \times 10^8$, about $1 \times 10^8$ to about $2.5 \times 10^8$, about $1.5 \times 10^8$ to about $2 \times 10^8$ total CD34+ cells. In some embodiments, the ex-vivo expanded CD133+/CD34+ cord blood fraction selected for transplantation has total post-expansion (post-culturing) CD34+ cell count of at least $5.6 \times 10^7$, at least $6 \times 10^7$, at least $8 \times 10^7$, at least $9 \times 10^7$, at least $1 \times 10^8$, at least $2 \times 10^8$, at least $3 \times 10^8$, at least $4 \times 10^8$ or at least $5 \times 10^8$ total CD34+ cells. In some embodiments, the ex-vivo expanded CD133+/CD34+ cord blood fraction selected for transplantation has total post-expansion (post-culturing) CD34+ cell count of at least $2 \times 10^8$ total CD34+ cells. In some embodiments, the ex-vivo expanded CD133+/CD34+ cord blood fraction selected for transplantation has total post-expansion (post-culturing) CD34+ cell count of at least $8 \times 10^7$ total CD34+ cells. In some embodiments, the ex-vivo expanded CD133+/CD34+ cord blood fraction selected for transplantation has total post-expansion (post-culturing) CD34+ cell count of at least $5.6 \times 10^7$ total CD34+ cells.

In particular embodiments, the ex-vivo expanded CD133+/CD34+ cord blood fraction selected for transplantation has total post-expansion (post-culturing) CD133+ cell count of about $2.4 \times 10^7$ to about $2 \times 10^8$ CD133+ cells. In some embodiments, the ex-vivo expanded CD133+/CD34+ cord blood fraction selected for transplantation has total post-expansion (post-culturing) CD133+ cell count of about $3 \times 10^7$ to about $1 \times 10^8$, about $5 \times 10^7$ to about $8 \times 10^7$, about $6 \times 10^7$ to about $7 \times 10^7$ total CD133+ cells. In some embodiments, the ex-vivo expanded CD133+/CD34+ cord blood fraction selected for transplantation has total post-expansion (post-culturing) CD133+ cell count of at least $2.4 \times 10^7$, at least $3.5 \times 10^7$, at least $5 \times 10^7$, at least $7 \times 10^7$, at least $8 \times 10^7$, at least $1\times10^8$, at least $1.5\times10^8$ or at least $2\times10^8$ total CD133+ cells. In some embodiments, the ex-vivo expanded CD133+/CD34+ cord blood fraction selected for transplantation has total post-expansion (post-culturing) CD133+ cell count of at least $2.4\times10^7$ total CD133+ cells. In some embodiments, the ex-vivo expanded CD133+/CD34+ cord blood fraction selected for transplantation has total post-expansion (post-culturing) CD133+ cell count of at least $4\times10^7$ total CD133+ cells. In some embodiments, the ex-vivo expanded CD133+/CD34+ cord blood fraction selected for transplantation has total post-expansion (post-culturing) CD133+ cell count of at least $7.5\times10^7$ total CD133+ cells. In some embodiments, the ex-vivo expanded CD133+/CD34+ cord blood fraction selected for transplantation has total post-expansion (post-culturing) CD133+ cell count of at least $1.2\times10^8$ total CD133+ cells.

In further embodiments, the ex-vivo expanded CD133+/CD34+ cord blood fraction selected for transplantation has total post-expansion (post-culturing) CD133+/CD38− cell count of about $8\times10^5$ to about $25\times10^5$ CD133+/CD38− cells. In some embodiments, the ex-vivo expanded CD133+/CD34+ cord blood fraction selected for transplantation has total post-expansion (post-culturing) CD133+/CD38− cell count of about $10\times10^5$ to about $22\times10^5$, about $13\times10^5$ to about $20\times10^5$ or about $15\times10^5$ to about $17\times10^5$ total CD133+/CD38− cells. In some embodiments, the ex-vivo expanded CD133+/CD34+ cord blood fraction selected for transplantation has total post-expansion (post-culturing) CD133+/CD38− cell count of at least $8\times10^5$, at least $10\times10^5$, at least $11.5\times10^5$, at least $13\times10^5$, at least $15\times10^5$, at least $18\times10^5$, at least $20.0\times10^5$, at least $22\times10^5$ or at least $25\times10^5$ total CD133+ cells. In some embodiments, the ex-vivo expanded CD133+/CD34+ cord blood fraction selected for transplantation has total post-expansion (post-culturing) CD133+/CD38− cell count of at least $13\times10^5$. In some embodiments, the ex-vivo expanded CD133+/CD34+ cord blood fraction selected for transplantation has total post-expansion (post-culturing) CD133+/CD38− cell count of at least $8\times10^5$. In some embodiments, the ex-vivo expanded CD133+/CD34+ cord blood fraction selected for transplantation has total post-expansion (post-culturing) CD133+/CD38− cell count of at least $10\times10^5$.

In yet further embodiments, the ex-vivo expanded CD133+/CD34+ cord blood fraction selected for transplantation has total post-expansion (post-culturing) CD14+ cell count of about $8\times10^7$ to about $15\times10^8$ CD14+ cells. In some embodiments, the ex-vivo expanded CD133+/CD34+ cord blood fraction selected for transplantation has total post-expansion (post-culturing) CD14+ cell count of about $10\times10^7$ to about $10\times10^8$, about $12\times10^7$ to about $8\times10^8$, about $15\times10^7$ to about $6\times10^8$, about $2\times10^8$ to about $5\times10^8$, or about $3\times10^8$ to about $4\times10^8$ CD14+ cells. In some embodiments, the ex-vivo expanded CD133+/CD34+ cord blood fraction selected for transplantation has total post-expansion (post-culturing) CD14+ cell count of at least $8\times10^7$, at least $10\times10^7$, at least $2\times10^8$, at least $4\times10^8$, at least $6\times10^8$, at least $8\times10^8$, at least $10.0\times10^8$, at least $12\times10^8$ or at least $15\times10^8$ total C14+ cells. In some embodiments, the ex-vivo expanded CD133+/CD34 cord blood fraction selected for transplantation has total post-expansion (post-culturing) CD14+ cell count of at least $8\times10^7$. In some embodiments, the ex-vivo expanded CD133+/CD34 cord blood fraction selected for transplantation has total post-expansion (post-culturing) CD14+ cell count of at least $2\times10^8$. In some embodiments, the ex-vivo expanded CD133+/CD34 cord blood fraction selected for transplantation has total post-expansion (post-culturing) CD14+ cell count of at least $7.5\times10^8$.

In yet further embodiments, the ex-vivo expanded CD133+/CD34+ cord blood fraction selected for transplantation has total post-expansion (post-culturing) CD15+ cell count of about $2\times10^8$ to about $2\times10^9$ CD15+ cells. In some embodiments, the ex-vivo expanded CD133+/CD34+ cord blood fraction selected for transplantation has total post-expansion (post-culturing) CD15+ cell count of about $2.5\times10^8$ to about $1.5\times10^9$, about $4\times10^8$ to about $0.5\times10^9$, about $6\times10^8$ to about $9\times10^8$ or about $7\times10^8$ to about $8\times10^8$ CD15+ cells. In some embodiments, the ex-vivo expanded CD133+/CD34+ cord blood fraction selected for transplantation has total post-expansion (post-culturing) CD15+ cell count of at least $2\times10^8$, at least $4\times10^8$, at least $6\times10^8$, at least $8\times10^8$, at least $1\times10^9$ or at least $2\times10^9$ total CD15+ cells. In some embodiments, the ex-vivo expanded CD133+/CD34 cord blood fraction selected for transplantation has total post-expansion (post-culturing) CD15+ cell count of at least $2\times10^8$. In some embodiments, the ex-vivo expanded CD133+/CD34 cord blood fraction selected for transplantation has total post-expansion (post-culturing) CD15+ cell count of at least $6\times10^8$. In some embodiments, the ex-vivo expanded CD133+/CD34 cord blood fraction selected for transplantation has total post-expansion (post-culturing) CD15+ cell count of at least $8.5\times10^8$. In some embodiments, the ex-vivo expanded CD133+/CD34 cord blood fraction selected for transplantation has total post-expansion (post-culturing) CD15+ cell count of at least $1.1\times10^9$.

In yet further embodiments, the ex-vivo expanded CD133+/CD34+ cord blood fraction selected for transplantation has total post-expansion (post-culturing) CD11b+ cell count of about $8\times10^7$ to about $8\times10^9$ CD11b+ cells. In some embodiments, the ex-vivo expanded CD133+/CD34+ cord blood fraction selected for transplantation has total post-expansion (post-culturing) CD11b+ cell count of about $1\times10^8$ to about $5\times10^9$, about $4\times10^8$ to about $2\times10^9$, about $6\times10^8$ to about $1\times10^9$ or about $8\times10^8$ to about $9\times10^8$ CD11b+ cells. In some embodiments, the ex-vivo expanded CD133+/CD34+ cord blood fraction selected for transplantation has total post-expansion (post-culturing) CD11b+ cell count of at least $8\times10^7$, at least $1\times10^8$, at least $4\times10^8$, at least $6\times10^8$, at least $8\times10^8$, at least $1\times10^9$, at least $2\times10^9$, at least $4\times10^9$, at least $6\times10^9$ or at least $8\times10^9$ total C11b+ cells. In some embodiments, the ex-vivo expanded CD133+/CD34 cord blood fraction selected for transplantation has total post-expansion (post-culturing) CD11b+ cell count of at least $8\times10^7$. In some embodiments, the ex-vivo expanded CD133+/CD34 cord blood fraction selected for transplantation has total post-expansion (post-culturing) CD11b+ cell count of at least $10\times10^7$. In some embodiments, the ex-vivo expanded CD133+/CD34 cord blood fraction selected for transplantation has total post-expansion (post-culturing) CD11b+ cell count of at least $2\times10^8$. In some embodiments, the ex-vivo expanded CD133+/CD34 cord blood fraction selected for transplantation has total post-expansion (post-culturing) CD11b+ cell count of at least $5\times10^8$. In some embodiments, the ex-vivo expanded CD133+/CD34 cord blood fraction selected for transplantation has total post-expansion (post-culturing) CD11b+ cell count of at least $3\times10^9$.

In some embodiments, the ex-vivo expanded CD133+/CD34+ cord blood fraction selected for transplantation has total post-expansion (post-culturing) CD1(a and c)+ cell count of about $3.2\times10^7$ to about $3\times10^8$ CD15+ cells. In some embodiments, the ex-vivo expanded CD133+/CD34+ cord blood fraction selected for transplantation has total post-expansion (post-culturing) CD1(a and c)+ cell count of about $4 \times 10^7$ to about $1 \times 10^8$, about $6 \times 10^7$ to about $9 \times 10^7$ or about $7 \times 10^7$ to about $8 \times 10^7$ CD1(a and c)+ cells. In some embodiments, the ex-vivo expanded CD133+/CD34+ cord blood fraction selected for transplantation has total post-expansion (post-culturing) CD1(a and c)+ cell count of at least $3.2 \times 10^7$, at least $4 \times 10^7$, at least $6 \times 10^7$, at least $8 \times 10^7$, at least $1 \times 10^8$ or at least $3 \times 10^8$ total CD1(a and c)+ cells. In some embodiments, the ex-vivo expanded CD133+/CD34+ cord blood fraction selected for transplantation has total post-expansion (post-culturing) CD1(a and c)+ cell count of at least $3.2 \times 10^7$. In some embodiments, the ex-vivo expanded CD133+/CD34+ cord blood fraction selected for transplantation has total post-expansion (post-culturing) CD1(a and c)+ cell count of at least $5 \times 10^7$. In some embodiments, the ex-vivo expanded CD133+/CD34+ cord blood fraction selected for transplantation has total post-expansion (post-culturing) CD1(a and c)+ cell count of at least $7.3 \times 10^7$. In some embodiments, the ex-vivo expanded CD133+/CD34+ cord blood fraction selected for transplantation has total post-expansion (post-culturing) CD1(a and c)+ cell count of at least $2.2 \times 10^8$.

Examples of exemplary post-expansion criteria for selection of cord blood units for ex-vivo transplantation into a subject are presented in Tables IX-XII hereinbelow.

TABLE IX

Selected, Expanded Cord Blood criteria for Transplantation

| Parameter | Value |
|---|---|
| Total viable cells | At least $12 \times 10^8$ |
| Viability | At least 76% |
| CD34+ cell fraction | At least 10% |
| Total CD34+ cells | At least $7 \times 10^7$ |
| Total CD133+ cells | At least $2.9 \times 10^7$ |
| Total CD133+/CD38− cells | At least $11 \times 10^5$ |
| Total CD14+ cells | At least $8 \times 10^7$ |
| Total CD15+ cells | At least $4 \times 10^8$ |
| Total CD11b+ cells | At least $1 \times 10^8$ |
| Total CD1(a and c)+ cells | At least $8 \times 10^7$ |

TABLE X

Selected, Expanded Cord Blood criteria for Transplantation

| Parameter | Value |
|---|---|
| Total viable cells | At least $8 \times 10^8$ |
| Viability | At least 70% |
| CD34+ cell fraction | At least 7% |
| Total CD34+ cells | At least $5.6 \times 10^7$ |
| Total CD133+ cells | At least $2.4 \times 10^7$ |
| Total CD133+/CD38− cells | At least $8 \times 10^5$ |
| Total CD14+ cells | At least $8 \times 10^7$ |
| Total CD15+ cells | At least $2 \times 10^8$ |
| Total CD11b+ cells | At least $8 \times 10^7$ |
| Total CD1 (a and c)+ cells | At least $3.2 \times 10^7$ |

TABLE XI

Selected, Expanded Cord Blood criteria for Transplantation

| Parameter | Value |
|---|---|
| Total viable cells | At least $8 \times 10^8$ |
| Viability | At least 80% |
| CD34+ cell fraction | At least 11% |
| Total CD34+ cells | At least $1 \times 10^8$ |

TABLE XI-continued

Selected, Expanded Cord Blood criteria for Transplantation

| Parameter | Value |
|---|---|
| Total CD133+ cells | At least $4 \times 10^7$ |
| Total CD133+/CD38− cells | At least $1.6 \times 10^6$ |
| Total CD14+ cells | At least $2 \times 10^8$ |
| Total CD15+ cells | At least $7 \times 10^8$ |
| Total CD11b+ cells | At least $1.3 \times 10^8$ |
| Total CD1(a and c)+ cells | At least $6 \times 10^7$ |

TABLE XII

Selected, Expanded Cord Blood criteria for Transplantation

| Parameter | Value |
|---|---|
| Total viable cells | At least $11 \times 10^8$ |
| Viability | At least 72% |
| CD34+ cell fraction | At least 11% |
| Total CD34+ cells | At least $6.7 \times 10^7$ |
| Total CD133+ cells | At least $5.8 \times 10^7$ |
| Total CD133+/CD38− cells | At least $9.3 \times 10^5$ |
| Total CD14+ cells | At least $11 \times 10^7$ |
| Total CD15+ cells | At least $6.9 \times 10^8$ |
| Total CD11b+ cells | At least $21 \times 10^7$ |
| Total CD1(a and c)+ cells | At least $9.2 \times 10^7$ |

As described hereinabove, parameters of safety and contamination are monitored to ensure that no ex-vivo expanded CD133+/CD34+ cord blood fractions having mycoplasma or bacterial, yeast or mold growth are selected for transplantation. Thus, in some embodiments, the ex-vivo expanded CD133+/CD34+ cord blood fractions selected for transplantation are free of bacterial, yeast, mold and mycoplasm following initiation of expansion, on day 7, on day 14 and at the completion of expansion.

In some embodiments, the ex-vivo expanded CD133+/CD34+ cells selected suitable for transplantation have at least $8 \times 10^8$ total viable cells, at least $5.6 \times 10^7$ total CD34+ cells, at least $2.4 \times 10^7$ total CD133+ cells, at least $8 \times 10^7$ total CD14+ cells, and at least $3.2 \times 10^7$ total CD1(a and c)+ cells. In further embodiments, the ex-vivo expanded CD133+/CD34+ cells selected suitable for transplantation have at least $10 \times 10^8$ total viable cells, at least 9% CD34+ cells, at least $5.6 \times 10^7$ total CD34+ cells, at least $4 \times 10^7$ total CD133+ cells, at least $2 \times 10^8$ total CD15+ cells, at least $10 \times 10^7$ total CD11b+ cells and at least $5 \times 10^7$ total CD1(a and c)+ cells.

In other embodiments, the ex-vivo expanded CD133+/CD34+ cells selected suitable for transplantation have at least $8 \times 10^8$ total viable cells, at least 70% viability of the cells, at least 7% CD34+ cells, at least $8 \times 10^5$ CD133+/CD38− cells, at least $2 \times 10^8$ total CD15+ cells and at least $8 \times 10^7$ total CD11b+ cells.

In further embodiments, the appearance of the ex-vivo expanded CD133+/CD34+ cord blood fraction is monitored. Observation of the expanded CD133+/CD34+ cell fraction is directed to color and texture of the fraction. In some embodiments, ex-vivo expanded CD133+/CD34+ cell fractions appearing yellowish, cloudy-to opaque with no white clumps or foreign particles are selected.

In some embodiments, the ex-vivo expanded CD133+/CD34+ cells selected suitable for transplantation are washed and suspended in a cryopreservation solution such as CryoStor® CS10 (BioLife Solutions, Inc.). The expanded CD133+/CD34+ fraction cell suspension is transferred into the cryopreservation bag (CryoMACS freezing bag, Miltenyi Biotech), labeled and frozen using a control rate freezer. The storage is done in liquid nitrogen (LN).

In some embodiments, the first, ex-vivo cultured CD133+/CD34+ selected cord blood fraction, and the second, unselected CD133/CD34 negative cord blood fraction are cryopreserved separately, in liquid nitrogen.

Transplantation of Expanded, Ex-Vivo Cultured CD133+/CD34+ Selected Cord Blood Fractions and Unselected CD133/CD34 Negative Cord Blood Fractions in a Subject Expanded selected CD133+/CD34+ cord blood fractions, and unselected CD133/CD34 negative fractions that have been selected suitable for transplantation by can be used for transplantation into subjects in need thereof. Any of the methods for selection of cord blood units for ex-vivo expansion described hereinabove, for expansion (ex-vivo culturing) of cord blood units described hereinabove, and/or for transplantation following ex-vivo expansion, and/or for cryopreservation of the cord blood fractions, and each of their embodiments taken alone or in various combinations may be used for affecting the methods for selecting cultured (ex-vivo expanded) CD133+/CD34+ selected and unselected, CD133/CD34 negative fractions as is described in this section and the sections that follow. It will be appreciated that the ex-vivo expanded CD133+/CD34+ and the uncultured CD133/CD34 negative cord blood cell fractions may be selected or excluded according to at least two, at least three, at least four, at least five, at least six, at least seven, at least eight, at least nine, at least ten or more, or according to all of the selection parameters disclosed herein.

In some embodiments, the subject in need of transplantation is suffering from a hematological disease. In some embodiments, the subject is suffering from a hematological malignancy.

It will be appreciated that the methods, compositions, kits and articles of manufacture of the present invention can be used to treat or ameliorate symptoms of other indications, including but not limited to chronic myeloid leukemia, other myeloproliferative disorders, multiple myeloma, aplastic anemia, pure red-cell aplasia, paroxysmal nocturnal hemoglobinuria, fanconi anemia, thalassemia major, sickle cell anemia, severe combined immunodeficiency (SCID), Wiskott-Aldrich syndrome, hemophagocytic lymphohistiocytosis, inborn errors of metabolism, epidermolysis bullosa, severe congenital neutropenia, Shwachman-Diamond syndrome, Diamond-Blackfan anemia, leukocyte adhesion deficiency, autoimmune diseases and metabolic disease.

In some embodiments, the ex-vivo expanded CD133+/CD34+ cells selected suitable for transplantation have at least $8\times10^8$ total viable cells, at least $2.4\times10^7$ total CD133+ cells, at least $2\times10^8$ total CD15+ cells, and at least $3.2\times10^7$ total CD1(a and c)+ cells.

In further embodiments, the ex-vivo expanded CD133+/CD34+ cells selected suitable for transplantation have at least $8\times10^8$ total viable cells, at least 83% viability of the cells, at least $2\times10^8$ total CD14+ cells, at least $1\times10^8$ total CD11b+ cells and at least $6\times10^7$ total CD1(a and c)+ cells.

In further embodiments, the ex-vivo expanded CD133+/CD34+ cells selected suitable for transplantation have at least $8\times10^8$ total viable cells, at least 83% viability of the cells, at least $2\times10^8$ total CD14+ cells, at least $1\times10^8$ total CD11b+ cells and at least $6\times10^7$ total CD1(a and c)+ cells.

In some embodiments, the ex-vivo expanded CD133+/CD34+ cells selected suitable for transplantation have at least 70% viability, at least $8\times10^5$ total CD133+/CD38− cells and at least $8\times10^7$ total CD11b+ cells.

In some embodiments, the ex-vivo expanded CD133+/CD34+ cells selected suitable for transplantation have at least $8\times10^8$ total viable cells, at least 70% viability, at least $8\times10^5$ total CD133+/CD38− cells and at least $8\times10^7$ total CD11b+ cells.

In further embodiments, the ex-vivo expanded CD133+/CD34+ cells selected suitable for transplantation have a total CD34+ fraction of at least 7%, at least $8\times10^7$ total CD14+ cells and at least $8\times10^7$ total CD11b+ cells.

Subjects

As used herein, a "subject" or "patient" can be any mammal, e.g., a human, a primate, mouse, rat, dog, cat, cow, horse, pig, sheep, goat, camel. In a specific embodiment, the subject is a human.

As used herein, a "subject in need thereof" is a subject having the need for transfusion, infusion or implantation of the cord blood fractions of the present invention to treat or ameliorate a disease, disorder or condition. In one embodiment, the subject has (been diagnosed with) or suffering from a hematological disease. In some embodiments, the hematological disease is a cell proliferative disorder. In other embodiments, the hematological disease is a hematological malignancy.

As used herein, the term "risk of" or "probability of" refers to the likelihood of an occurrence. In some embodiments, the risk or probability of an occurrence (e.g engraftment or non-engraftment of a cord blood graft, non-relapse mortality, and the like) in an individual refers to a risk calculated from comparative data between groups receiving treatment compared to groups not receiving the same treatment. In some embodiments, an increased or decreased risk or probability reflects the difference between treatment and control groups with respect to the outcome under consideration. In some embodiments, an increase or decrease in the risk or probability of a particular occurrence or condition is only relative, and not expressed in numerical values.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. In specific embodiments, the methods provided herein are used to treat or alleviate a symptom of cancer. The term "cancer" includes solid tumors, as well as, hematologic tumors and/or malignancies. In preferred embodiments, the subject has (been diagnosed with) or suffering from a hematologic malignancy. The hematologic malignancy can be selected from the group consisting of acute lymphoblastic leukemia (ALL), acute myelogenous leukemia (AML), chronic myelogenous leukemia (CML), myelodysplastic syndrome (MDS), non-Hodgkin's lymphoma or Hodgkin's disease.

In further embodiments, the ex-vivo expanded CD133+/CD34+ cells selected suitable for transplantation have at least $8\times10^8$ total viable cells, at least 75% viability of the cells, at least 7% CD34+ cells, at least $8.1\times10^7$ total CD34+ cells, at least 6×10⁷ total CD133+ cells, at least 3×10⁸ total CD15+ cells, at least 8.7×10⁷ total CD11b+ cells and at least 5×10⁷ total CD1(a and c)+ cells.

In some embodiments, the ex-vivo expanded CD133+/CD34+ cells selected suitable for transplantation have at least 8×10⁸ total viable cells, at least 7% CD34+ cells, at least 8×10⁵ CD133+/CD38− cells, at least 2×10⁸ total CD15+ cells, and at least 8×10⁷ total CD11b+ cells.

In some embodiments, the methods and compositions and kits of the present invention can be used for treatment of subjects of all age groups. In specific embodiments, the subject or patient is between 16-60 years of age.

In some embodiments, the ex-vivo expanded CD133+/CD34+ cells selected suitable for transplantation have at least 8×10⁸ total viable cells, at least 2.4×10⁷ total CD133+ cells and at least 5.6×10⁷ total CD34+ cells.

In further embodiments, the ex-vivo expanded CD133+/CD34+ cells selected suitable for transplantation have at least 10×10⁸ total viable cells, at least 83% viability of the cells and at least 7×10⁷ total CD1(a and c)+ cells.

In some embodiments, the ex-vivo expanded CD133+/CD34+ cells selected suitable for transplantation have a CD34+ cell fraction of at least 7%, at least 8×10⁵ total CD133+/CD38− cells and at least 8×10⁷ total CD14+ cells.

In some embodiments, the subject in need thereof can have acute lymphoblastic leukemia (ALL) at one of the following stages: (a) high risk first complete morphologic remission (CR1), defined as one or more of the following: presence of t(4;11), t(9;22), t(1;19) or MLL rearrangements t(11q23); extreme leukocytosis (WBC>30,000/µl for B-ALL or >100,000/µl for T-ALL); Failure to achieve complete morphological remission after first induction therapy; Minimal Residual Disease (MRD) at screening by flow cytometry, or (b) second or subsequent remission.

The subject in need thereof can have acute myelogenous leukemia (AML) at one of the following stages: (a) First complete morphologic remission (CR1) that is not considered a favorable risk, favorable risk being defined as one or more of the following and absence of MRD at screening: t(8;21) without cKIT mutation; inv(16) or t(16;6) without cKIT mutation, normal karyotype with mutated NPM1 and no FLT-3 Internal Tandem Duplication; normal karyotype with double mutated CEBPA; APL in first or second molecular remission at end of consolidation, or (b) second or subsequent remission.

In some embodiments, the ex-vivo expanded CD133+/CD34+ cells selected suitable for transplantation have at least 8×10⁸ total viable cells, at least 70% viability of the cells, at least 8×10⁷ total CD14+ cells and at least 3.2×10⁷ total CD1(a and c)+ cells.

In further embodiments, the ex-vivo expanded CD133+/CD34+ cells selected suitable for transplantation have a total CD34+ fraction of at least 7%, at least 8×10⁷ total CD14+ cells and at least 8×10⁷ total CD11b+ cells.

In further embodiments, the ex-vivo expanded CD133+/CD34+ cells selected suitable for transplantation have at least 8×10⁸ total viable cells, at least 83% viability of the cells, at least 2×10⁸ total CD14+ cells, at least 1×10⁸ total CD11b+ cells and at least 6×10⁷ total CD1(a and c)+ cells.

The subject in need thereof can have chronic myelogenous leukemia (CML) at one of the following stages: (a) Chronic phase with one or more of the following characteristics: Failure to achieve a rimaryhematological or cytogenic response to either nilotinib or dasatinib (following European Leukemia Net timelines). Intolerance to/failure of two tyrosine kinase inhibitors (TKI), and any T315I mutation; (b) Accelerated phase with one or more of the following characteristics: Newly diagnosed patient not achieving optimal response to TKIs as outlined in European LeukemiaNet timelines; TKI patients progressing from chronic phase, or (c) a Prior blast crisis (myeloid and lymphoid) currently in complete morphological remission.

The subject in need thereof can have Myelodysplastic Syndrome (MDS) with International Prognostic Scoring System (IPSS) risk category of INT-1 or greater. On screening morphologic analysis patients have no circulating myeloblasts and ≤10% myeloblasts in the bone marrow. MDS patients categorized as INT-1 on primary presentation have life threatening neutropenia (ANC<0.5×109/L) or thrombocytopenia (platelets <30×109/L).

The subject in need thereof can have Non-Hodgkin's lymphoma or Hodgkin's disease with at least one of the following features: (a) progressed or non-responsive to upfront chemotherapy and has achieved a partial remission (partial remission defined as ≥50% reduction of disease from the prior course of chemotherapy) to subsequent therapy or (b) second or subsequent complete or partial remission (partial remission defined as ≥50% reduction of disease from the prior course of chemotherapy) and not appropriate candidates for autologous stem cell transplantation.

In some embodiments, the ex-vivo expanded CD133+/CD34+ cells selected suitable for transplantation have at least 70% viability of the cells, at least 7% CD34+ cells, at least 2.4×10⁷ total CD133+ cells, at least 8×10⁷ total CD14+ cells and at least 3.2×10⁷ total CD1(a and c)+ cells. In some embodiments, the ex-vivo expanded CD133+/CD34+ cells selected suitable for transplantation have at least 8×10⁸ total viable cells, at least 2×10⁸ total CD15+ cells and at least 8×10⁷ total CD11b+ cells.

In some embodiments, a subject in need thereof can be defined according to the following criteria: a performance score of at least 70% by Karnofsky, and sufficient physiologic reserves including: a. Cardiac: Left ventricular ejection fraction (LVEF) of ≥40% by echocardiogram, radionuclide scan or cardiac MRI; b. Pulmonary function tests demonstrating FVC and FEV1 of >50% of predicted for age and cDLCO>50% of predicted; c. Renal: Creatinine clearance test (by Cockcroft-Gault equation) ≥60 mL/min, and d. Hepatic: Serum Bilirubin <2.0 mg/dl; Hepatic transaminases (ALT and AST)<3×upper limit of normal range In some embodiments, subjects can be excluded from consideration for treatment for any of the following:
1. MDS or CML with "marked" or "3+" fibrosis;
2. CMMoL or MDS/CMMoL overlap;
3. Fewer than 21 days elapsed since initiation of the patient's last chemotherapy cycle and the initiation of the stem cell transplant preparative regimen (intrathecal agents, hydroxyurea, tyrosine kinase inhibitors, hypomethylating agents, rituximab and lenalidomide not considered chemotherapy);
4. Persistent clinically significant toxicities that make the patient unsuitable for transplant;
5. Evidence of anti-HLA antibodies to a candidate cord blood unit profile (MFI>3000 to HLA A, B, C, or DRB1);
6. Evidence of HIV infection or HIV positive serology;
7. Evidence of active Hepatitis B, Hepatitis C or EBV as determined by serology or PCR;
8. Pregnancy, as indicated by a positive serum human chorionic gonadotrophin (HCG) test, or lactation;
9. Active malignancy other than that for which the UCB transplant is being performed within 12 months of enrollment in treatment program. Fully resected cutaneous squamous cell or basal cell carcinoma or cervical carcinoma in situ within 12 months of enrollment is permitted;

10. Evidence of uncontrolled bacterial, fungal or viral infections or severe concomitant diseases, which indicate that the patient could not tolerate transplantation;

11. Patients with signs and symptoms of leukemic blasts in the central nervous system (CNS);

12. Patients with an 8/8 allele level HLA-matched and readily available related or unrelated donor (whose stem cells can be collected in a timely manner without jeopardizing recipient outcome);

13. Prior allogeneic hematopoietic stem cell transplant;

14. Allergy to bovine products, gentamicin, or to any other product that may interfere with the treatment;

15. Psychologically incapable of undergoing bone marrow transplant (BMT) with associated strict isolation or documented history of medical non-compliance and/or psychiatric illness and/or social situations that would limit compliance with treatment requirements, and 16. Enrolled in an interventional clinical trial or received an investigational treatment within 30 days prior to the approved date of treatment.

In some embodiments, the subject in need thereof has been subjected to myeloablative therapy or conditioning regime. In specific embodiments, the subject has been subjected to myeloablative therapy or conditioning regime prior to transplantation or administration of the compositions of the present invention. The subject can be subjected to the myeloablative therapy or conditioning regime between 11 days (−11) to 2 days (−2) prior to transplantation or administration of the compositions of the present invention, or, in another regimen, between 8 days (−8) to 1 day (−1) prior to transplantation or administration of the compositions of the present invention, or between 7 days (−7) to 3 days (−3) prior to transplantation or administration of the compositions of the present invention. The myeloablative therapy or conditioning regime can include total body irradiation (TBI) and fludarabine, and may also include Busulfan, cyclophosphamide or Thiotepa. In one regimen, total radiation dose will be 1350 cGy in 8 or 9 fractions over 5 days. Two fractions on the same day will be given at a minimum of 6 hours apart from beam on to beam on, for example, on days −9 to −5 of the 11-day regimen. In the 11 day regimen, fludarabine (40 mg/m$^2$/day) will be administered IV, for example, on days −5 to −2. Fludarabine will be dosed as per adjusted ideal body weight. In the 11 day regimen, Thiotepa (5 mg/kg) is administered IV on days −11 and −10.

In an 8 day regimen, total radiation dose will be 1350 cGy in 8 fractions over 4 days, two fractions on the same day will be given at a minimum of 6 hours apart from beam on to beam on, on days −4 to −1. Fludarabine 25 mg/m$^2$/day is administered over 60 minutes IV infusion on days −8 through −6. Fludarabine will be dosed as per adjusted ideal body weight. In some embodiments, the regime can also include cyclophosphamide. Cyclophosphamide can be administered at 60 mg/Kg/day as per adjusted ideal body weight, for example, on days −8 and −7 of the 8 day regimen.

Some conditioning regimen do not include TBI. In an exemplary 7 day regimen, Thiotepa (5 mg/kg) is administered intravenously on days −7 and −6, and Busulfan (3.2 mg/kg or adjusted for cumulative Busulfan exposure of 75 mg*h/L after 3 days) is administered intravenously on days −5 to −4. In such a regimen, fludarabine 50 mg/m$^2$/day is administered over 60 minutes in IV infusions on days −5 through −3.

In some embodiments, the subject in need thereof has been subjected to graft-versus-host disease (GvHD) prophylaxis regime. In one embodiment, the subject has been subjected to GvHD prophylaxis regime prior to transplantation or administration of the compositions of the present invention. The subject can be subjected to the GvHD prophylaxis regime between 9 days (−9) to 1 day (−1) prior to transplantation or administration of the compositions of the present invention. In other embodiments, the subject has the GvHD prophylaxis regime at least 3 days prior (−3) to transplantation or administration of the compositions of the present invention, to at least day +150. The subject can be subjected to either myeloablative therapy or conditioning regime or GvHD prophylaxis regime individually, or in combination. The GvHD prophylaxis regime can include mycophenolate mofetil (MMF) and tacrolimus. In some embodiments, tacrolimus is administered via IV from day −3 until oral medications are tolerated, then PO through day +150 to target blood level of 5-15 ng/ml and MMF is administered 1 g TID via IV or PO (15 mg/kg IV TID if patient weighs <50 kg) beginning day −3 to at least day +60.

In some embodiments, subjects in need thereof will have an appropriate long-term central venous access placed prior to the conditioning regimen. In some embodiments, the subjects will have a triple lumen tunneled catheter.

In some embodiments, subjects can receive any or all of the following: infusion support (e.g. diphenylhydramine or dexchlorpheniramine, hydrocortisone and acetaminophen), supportive cytokines (e.g. G-CSF), blood products as needed, anti-viral, anti-bacterial, PCP and/or fungal prophylaxis, CMV, EBV and HHV6 surveillance and IV immunoglobulin as needed.

In some embodiments, subjects receive any or all of an additional treatment for the hematological disease. Said treatment can be a treatment selected from the group consisting of an immunosuppressive treatment, chemotherapy and radio-therapy.

Thus, in some embodiments there is provided a method of treating a hematological disease in a subject in need thereof, the method comprising:

(a) separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells;

(b) ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM;

(c) cryopreserving said ex-vivo cultured first, CD133+/CD34+ selected blood cell fraction and said uncultured second, unselected blood cell fraction from step (b), (d) thawing said ex-vivo cultured first selected and said uncultured second, unselected blood cell fractions, and (e) transplanting the thawed ex-vivo cultured first selected and uncultured second unselected blood cell fractions from step (d) into a subject in need thereof, thereby treating said hematological disease in said subject.

In some embodiments, the method of treating a hematological disease in a subject in need thereof consists of:

(a) separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells;

(b) ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM;

(c) cryopreserving said ex-vivo cultured first, CD133+/CD34+ selected blood cell fraction and said uncultured second, unselected blood cell fraction from step (b), (d) thawing said ex-vivo cultured first selected and said uncultured second, unselected blood cell fractions, and (e) transplanting the thawed ex-vivo cultured first selected and uncultured second unselected blood cell fractions from step (d) into a subject in need thereof, thereby treating said hematological disease in said subject.

In some embodiments, the single umbilical cord blood unit suitable for transplantation is characterized by the following pre-cryopreservation parameters:

(i) at least $8 \times 10^6$ total CD34+ cells;
(ii) HLA-matched at least 4 out of 6 HLA class I (HLA-A and HLA-B, low resolution) and HLA class II (HLA-DRB1, high resolution) loci with said subject;
(iii) about $1.8 \times 10^9$ to about $3.0 \times 10^9$ pre-cryopreserved total nucleated cells, and
(iv) about $1.5 \times 10^7$ to about $3.0 \times 10^7$ pre-cryopreserved total nucleated cells per kilogram subject weight.

In a particular embodiment, the first cryopreserved ex-vivo cultured selected and said uncultured second, unselected blood cell fractions are thawed on the same day of transplantation. In some embodiments, The first cryopreserved ex-vivo cultured (expanded) CD133+/CD34+ fraction is kept frozen until the day of transplantation. On the day of transplantation, at the clinical site, first cryopreserved ex-vivo cultured (expanded) CD133+/CD34+ fraction is thawed and reconstituted with the infusion solution (8% w/v Human Serum Albumin (HSA) and 6.8% w/v Dextran-40) in a closed system.

In some embodiments, the unselected, CD133/CD34 negative cord blood fraction of the same cord blood unit is the fraction of cells which is eluted during the separation (e.g. CliniMACS positive separation) of CD133+ cells. This fraction contains the entire repertoire of immune cells, such as B, T and NK cells. The cells are washed and suspended in cryopreservation solution, CryoStor® CS10 (BioLife Solutions, Inc.) after elution from the selection column (e.g. CliniMACS column), labeled and then frozen using a control rate freezer. The storage is done in liquid nitrogen. The unselected CD133/CD34 negative fraction is kept frozen until the day of transplantation into the subject. On the day of transplantation, the unselected, CD133/CD34 negative fraction is thawed and reconstituted with the infusion solution (8% w/v HSA and 6.8% w/v Dextran-40) in a closed system. In some embodiments, the infusion solution is screened for suitability for use with the methods and compositions of the present invention. Exemplary criteria for selection of suitable infusion solution include safety tests indicating no bacterial, yeast or mold growth, endotoxin content of less than 0.5 Eu/ml and a clear, foreign particle-free appearance.

In some embodiments, the infusion solution is stored in bags until use (e.g. transplantation) at 2-8° C.

In some specific embodiments, transplantation of cord blood fractions is preceded by a safety assessment of the subject in need thereof on the day of transplantation, typically including a physical examination, CBC, blood chemistry (e.g at least serum creatinine, total bilirubin, alkaline phosphatase, AST, ALT and magnesium), Vital Signs: weight, temperature, blood pressure, pulse, and respiratory rate, and administration of concomitant medication, including RBC and platelet transfusions.

Infusion of the selected, expanded CD133+CD34+ and the unselected, CD133CD34 negative cord blood fractions into the subject in need thereof is typically done by transfusion via the patient's central venous catheter, subject to the limitations of individual site practice. In some embodiments, the selected, expanded CD133+/CD34+ cord blood fraction is infused first, followed immediately by the infusion of the unselected, CD133/CD34 negative (unmanipulated) cord blood fraction. In other embodiments, the unselected, CD133/CD34 negative (unmanipulated) cord blood fraction is infused first, followed immediately by the infusion of the selected, expanded CD133+/CD34+ cord blood fraction.

Thus, in some embodiments, of the present invention, transplantation is affected by infusion in an infusion solution into said patient, wherein said ex-vivo cultured first selected blood cell fraction is infused prior to said uncultured second, unselected blood cell fraction, while in other embodiments uncultured the second, unselected blood cell fraction is infused prior to said ex-vivo cultured first selected blood cell fraction.

As detailed hereinabove, both the selected, expanded CD133+/CD34+ cord blood fraction and the unselected, CD133/CD34 negative (unmanipulated) cord blood fraction selected suitable for transplantation are screened, inter alia, for total viable cell content. In some embodiments, the first ex-vivo cultured CD133+CD34+ blood cell fraction for infusion into the subject comprises at least $8 \times 10^8$ total viable cells. In some embodiments the second uncultured CD133/CD34 negative blood cell fraction for infusion into the subject comprises at least $4 \times 10^8$ total viable cells.

The method of treatment of hematological disease of the present invention can be used to treat hematological malignancies, including, but not limited to Chronic myelogenous leukemia (CML), acute lymphoblastic leukemia (ALL), acute myelogenous leukemia (AML) and myelodysplastic syndrome (MDS). Also contemplated is treatment of Hodgkin's Disease and non-Hodgkin's Lymphoma. As used herein, the term "treating a hematological disease" or "treating a hematological malignancy" refers to reducing the symptoms or signs of the hematological disease. In some embodiments, treating hematological diseases or a hematological malignancy is assessed according to, but not exclusively, reduction in symptoms over time, improvement in clinical parameters such as neutrophil and platelet count, reduced hospitalization and reduced risk of relapse or mortality.

Thus, according to some embodiments of the method of the present invention, separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells; ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM; cryopreserving said ex-vivo cultured first, CD133+/CD34+ selected blood cell fraction and said uncultured second, unselected blood cell fraction; thawing said ex-vivo cultured CD133+/CD34+ first selected and said uncultured CD133/CD34 negative second, unselected blood cell fractions, and transplanting the thawed ex-vivo cultured first selected and uncultured second unselected blood cell fractions into a subject in need thereof decreases time from transplantation to neutrophil engraftment in said subject, when compared to transplantation of a single or double unit of unmanipulated cord blood.

As used herein, the term "unmanipulated cord blood" refers to cord blood that has not undergone selection, and or expansion as described herewith. In some embodiments, unmanipulated cord blood is a fresh unit or a cryopreserved cord blood unit from the cord blood bank.

In some embodiments, transplantation of said first ex vivo cultured CD133+/CD34+ blood cell fraction and said second uncultured CD133−/CD34− blood decreases the time to neutrophil engraftment by 5-14 days when compared to transplantation of a single or double unit of unmanipulated cord blood.

As used herein, the term "neutrophil engraftment" refers to achieving an absolute neutrophil count (ANC)≥$0.5\times10^9$/L on 3 consecutive measurements on different days with subsequent donor chimerism (≤10% host cells by peripheral blood chimerism), on or before 42 days post transplant (and prior to infusion of any additional stem cells product). In some embodiments, decreasing the time to neutrophil engraftment refers to achieving an absolute neutrophil count (ANC)≥$0.5\times10^9$/L on 3 consecutive measurements on different days with subsequent donor chimerism (≤10% host cells by peripheral blood chimerism), on or before 16 days post transplant.

According to some embodiments of the method of the present invention, separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells; ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM; cryopreserving said ex-vivo cultured first, CD133+/CD34+ selected blood cell fraction and said uncultured second, unselected blood cell fraction; thawing said ex-vivo cultured CD133+/CD34+ first selected and said uncultured CD133/CD34 negative second, unselected blood cell fractions, and transplanting the thawed ex-vivo cultured first selected and uncultured second unselected blood cell fractions into a subject in need thereof decreases the time from transplantation to platelet engraftment in said subject, when compared to transplantation of a single or double unit of unmanipulated cord blood.

In other embodiments, transplantation of said first ex vivo cultured CD133+/CD34+ hematopoietic stem/progenitor blood cell fraction and said second uncultured CD133−/CD34− blood cell fraction increases the probability of platelet engraftment in said subject at 42 days post transplantation when compared to transplantation of a single or double unit of unmanipulated cord blood.

In specific embodiments, the term "platelet engraftment" relates to the first day of a minimum of 3 consecutive measurements on different days such that the patient has achieved a platelet count >$20\times10^9$/L with no platelet transfusions in the preceding 7 days (count day of engraftment as one of the preceding 7 days). The first day of the three measurements will be designated the day of platelet engraftment and occurs prior to any infusion of a second stem cell product.

According to some embodiments of the method of the present invention, separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells; ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM; cryopreserving said ex-vivo cultured first, CD133+/CD34+ selected blood cell fraction and said uncultured second, unselected blood cell fraction; thawing said ex-vivo cultured CD133+/CD34+ first selected and said uncultured CD133/CD34 negative second, unselected blood cell fractions, and transplanting the thawed ex-vivo cultured first selected and uncultured second unselected blood cell fractions into a subject in need thereof decreases the probability of non-engraftment by day 42 after transplantation in said subject, when compared to transplantation of a single or double unit of unmanipulated cord blood. In specific embodiments, the term "primary graft failure", or "non-engraftment" relates to failure to achieve neutrophil engraftment by day 42, as described hereinabove. Requirement for infusion of a second stem cell product to the subject on or prior to day 42 following transplantation is also considered primary graft failure. However, need for infusion of an additional stem cell product after documented neutrophil engraftment can be considered secondary graft failure, even if it occurs on or prior to day 42 post transplantation. The date of primary graft failure will be designated as day 43 post transplant.

In other embodiments, transplantation of said first ex vivo cultured CD133+/CD34+ blood cell fraction and said second uncultured CD133−/CD34− blood cell fraction into a subject in need thereof according to the methods of the present invention decreases the probability of secondary graft failure or secondary non engraftment when compared to transplantation of a single or double unit of unmanipulated cord blood. In specific embodiments, the term "secondary graft failure", or "non-engraftment" relates to documented neutrophil engraftment, followed by severe neutropenia (<$0.5\times10^9$/L for three or more consecutive laboratory values on separate days) with marrow cellularity <5%, without subsequent improvement occurring either spontaneously or after growth factor treatment. Infusion of an additional stem cell product after documented neutrophil engraftment is considered secondary graft failure. The earlier of the first day of severe neutropenia, as defined above, or the date of additional stem cell infusion will be designated the date of secondary graft failure.

According to some embodiments of the method of the present invention, separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells; ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM;

cryopreserving said ex-vivo cultured first, CD133+/CD34+ selected blood cell fraction and said uncultured second, unselected blood cell fraction; thawing said ex-vivo cultured CD133+/CD34+ first selected and said uncultured CD133/CD34 negative second, unselected blood cell fractions, and transplanting the thawed ex-vivo cultured first selected and uncultured second unselected blood cell fractions into a subject in need thereof decreases the probability of non-relapse mortality after transplantation in said subject, when compared to transplantation of a single or double unit of unmanipulated cord blood. As used herein, the term "non-relapse mortality" refers to any death not preceded by relapse of the subject's hematological disease or diseases.

In some embodiments, transplantation of said first ex vivo cultured CD133+/CD34+ blood cell fraction and said second uncultured CD133−/CD34− blood cell fraction decreases the probability of non-relapse mortality at 180-210 days after transplantation, when compared to transplantation of a single or double unit of unmanipulated cord blood.

In some embodiments, transplantation of said first ex vivo cultured CD133+/CD34+ blood cell fraction and said second uncultured CD133−/CD34− blood cell fraction decreases the risk of non-relapse mortality at 1 year when compared to transplantation of a single or double unit of unmanipulated cord blood. In some embodiments, transplantation of said first ex vivo cultured CD133+/CD34+ blood cell fraction and said second uncultured CD133−/CD34− blood cell fraction according to the methods of the present invention decreases the risk of non-relapse mortality at 15 months post transplantation year when compared to transplantation of a single or double unit of unmanipulated cord blood.

According to some embodiments of the method of the present invention, separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells; ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM; cryopreserving said ex-vivo cultured first, CD133+/CD34+ selected blood cell fraction and said uncultured second, unselected blood cell fraction; thawing said ex-vivo cultured CD133+/CD34+ first selected and said uncultured CD133/CD34 negative second, unselected blood cell fractions, and transplanting the thawed ex-vivo cultured first selected and uncultured second unselected blood cell fractions into a subject in need thereof decreases duration of hospitalization in said subject in the first 100 days post-transplantation, when compared to transplantation of a single or double unit of unmanipulated cord blood. As used herein, the term "duration of hospitalization" refers to the total number of days from transplant to the first discharge from the hospital.

In some embodiments, transplantation of the first ex vivo cultured CD133+/CD34+ blood cell fraction and said second uncultured CD133−/CD34− blood cell fraction decreases duration of post-transplantation hospitalization by 5-30 days, when compared to transplantation of a single or double unit of unmanipulated cord blood. In some embodiments, transplantation of the first ex vivo cultured CD133+/CD34+ blood cell fraction and said second uncultured CD133−/CD34− blood cell fraction increases the number of days alive and out of hospital following transplantation, when compared to transplantation of a single or double unit of unmanipulated cord blood. Days alive and out of the hospital, as used herein, are defined as a full days (calendar days) in which the patient was alive and not hospitalized.

According to some embodiments of the method of the present invention, separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells; ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM; cryopreserving said ex-vivo cultured first, CD133+/CD34+ selected blood cell fraction and said uncultured second, unselected blood cell fraction; thawing said ex-vivo cultured CD133+/CD34+ first selected and said uncultured CD133/CD34 negative second, unselected blood cell fractions, and transplanting the thawed ex-vivo cultured first selected and uncultured second unselected blood cell fractions into a subject in need thereof decreases risk of grade 2/3 bacterial or invasive fungal infections post-transplantation in said subject, when compared to transplantation of a single or double unit of unmanipulated cord blood. Grading of bacterial and/or invasive fungal infections is well known in the art. Signs of Grade 3 bacterial infections include, but are not limited to Bacteremia with deep organ involvement (e.g. with new or worsening pulmonary infiltrates; endocarditis), Severe sepsis with bacteremia, Fasciitis requiring debridement, Pneumonia requiring intubation, Brain abscess or meningitis without bacteremia and *Difficile* toxin positive stool with toxic dilatation or renal insufficiency with/without diarrhea. Signs of Grade 3 fungal infections include, but are not limited to Fungemia including Candidemia, Proven or probable invasive fungal infections (e.g., *Aspergillus, Mucor, Fusarium, Scedosporium*), Disseminated infections (defined as multifocal pneumonia, presence of urinary or blood antigen, and/or CNS involvement) with Histoplasmosis, Blastomycosis, Coccidiomycosis, or *Cryptococcus* and *Pneumocystis jiroveci* pneumonia (regardless of PaO2 level).

In some embodiments, transplantation of the first ex vivo cultured CD133+/CD34+ blood cell fraction and said second uncultured CD133−/CD34− blood cell fraction according to the methods of the present invention decreases risk of grade 2/3 bacterial or invasive fungal infections post-transplantation decreases risk of grade 2/3 bacterial or invasive fungal infections by 100 days post-transplantation in said subject, when compared to transplantation of a single or double unit of unmanipulated cord blood.

According to some embodiments of the method of the present invention, separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells; ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM; cryopreserving said ex-vivo cultured first, CD133+/CD34+ selected blood cell fraction and said uncultured second, unselected blood cell fraction; thawing said ex-vivo cultured CD133+/CD34+ first selected and said uncultured CD133/CD34 negative second, unselected blood cell fractions, and transplanting the thawed ex-vivo cultured first selected and uncultured second unselected blood cell fractions into a subject in need thereof decreases the risk of acute graft-versus-host disease grade III-IV in said subject at 100 days post transplantation, when compared to transplantation of a single or double unit of unmanipulated cord blood. In some embodiments, transplantation of the first ex vivo cultured CD133+/CD34+ blood cell fraction and said second uncultured CD133−/CD34− blood cell fraction according to the methods of the present invention decreases the risk of acute graft-versus-host disease grade III-IV in said subject at 180 days post transplantation in said subject, when compared to transplantation of a single or double unit of unmanipulated cord blood.

In some embodiments, transplantation of the first ex vivo cultured CD133+/CD34+ blood cell fraction and said second uncultured CD133−/CD34− blood cell fraction according to the methods of the present invention decreases the risk of chronic graft-versus-host disease (mild/moderate/severe) in said subject at 180 days or 1 year post transplantation in said subject, when compared to transplantation of a single or double unit of unmanipulated cord blood.

As used herein the term "acute GvHD" refers to acute Graft versus Host Disease, occurring earlier following transplantation, and chronic or cGvHD refers to chronic Graft versus Host Disease, present later, after the cut off point of Acute GvHD post-transplantation. In some embodiments, acute GvHD is classified according to the Consensus Conference on Acute GvHD grading (see Przepiorka et al, Bone Marrow Transplant 1995, 15:825-828), and cGvHD is classified according to the NIH consensus criteria for grading cGvHD (see Jagasia et al, Biol. Blood Marrow Transplant, 2015 21:389-401).

In some embodiments, of the method of the present invention, separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells; ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM; cryopreserving said ex-vivo cultured first, CD133+/CD34+ selected blood cell fraction and said uncultured second, unselected blood cell fraction; thawing said ex-vivo cultured CD133+/CD34+ first selected and said uncultured CD133/CD34 negative second, unselected blood cell fractions, and transplanting the thawed ex-vivo cultured first selected and uncultured second unselected blood cell fractions into a subject in need thereof increases the probability of disease-free survival by 15 months post transplantation, increases the probability of overall survival by 210 days, and/or 15 months post transplantation, improves immune reconstitution (numbers and proportions of different lymphocyte subpopulations) in said subject, for example, by 28, 70, 100, 180 and 365 days post transplantation, when compared to transplantation of a single or double unit of unmanipulated cord blood.

In some embodiments of the method of the present invention, separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells; ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM; cryopreserving said ex-vivo cultured first, CD133+/CD34+ selected blood cell fraction and said uncultured second, unselected blood cell fraction; thawing said ex-vivo cultured CD133+/CD34+ first selected and said uncultured CD133/CD34 negative second, unselected blood cell fractions, and transplanting the thawed ex-vivo cultured first selected and uncultured second unselected blood cell fractions into a subject in need thereof decreases the probability of disease relapse and relapse mortality in said subject post transplantation, when compared to transplantation of a single or double unit of unmanipulated cord blood.

In some embodiments, disease relapse is defined according to the following criteria:

Relapse of malignancy—Relapse is defined by either morphological or cytogenetic evidence of AML, ALL, CML, or MDS consistent with pre-transplant features.

Minimal residual disease—minimal residual disease (MRD) is defined by the sole evidence of malignant cells by flow cytometry, or fluorescent in situ hybridization (FISH), or Southern blot or Western blot, or polymerase chain reaction (PCR), or other techniques, in the absence of morphological or cytogenetic evidence of disease in blood or marrow. Evidence of minimal residual disease alone is not sufficient to meet the definition of relapse, however, minimal residual disease that progresses can be considered as relapse.

Acute Leukemia—Relapse can be defined as any of the following:

>5% blasts in the marrow, not attributed to other causes (e.g., bone marrow regeneration)

The appearance of new dysplastic changes within the bone marrow, not attributed to other causes.

Reappearance of leukemic blasts in the peripheral blood.

Reappearance of previous cytogenetic or molecular marker of disease present prior to transplantation.

The development of extramedullary leukemia or leukemic cells in the cerebral spinal fluid.

Institution of any therapy in response to detection of MRD, including withdrawal of immunosuppressive therapy or the addition of tyrosine kinase inhibitors or hypomethylating agents, will be considered evidence of relapse regardless of whether the criteria described above are met.

Chronic Myelogenous Leukemia (CML)

Hematologic relapse can be diagnosed when:

1. Immature hematopoietic cells are persistently documented in the peripheral blood; or, 2. There is myeloid hyperplasia in the bone marrow in the presence of cytogenetic relapse.

Cytogenetic relapse can be diagnosed when:

1. 50% of the metaphases exhibit the characteristic (9;22) translocation with at least ten metaphases analyzed; or, 2. At least one metaphase exhibits the (9;22) translocation on each of two separate consecutive examinations at least one month apart, regardless of number of metaphases analyzed. The date of the earliest test will be considered the date of relapse.

MDS

Relapse can be defined as any of the following:

Satisfying above criteria for evolution into acute leukemia; or,

Reappearance of pre-transplant morphologic abnormalities, detected in two consecutive bone marrow specimens taken at least one month apart (the date of the earliest test will be considered the date of relapse); or, Reappearance of pre-transplant cytogenetic abnormality in at least one metaphase on each of two separate consecutive examinations at least one month apart, regardless of the number of metaphases analyzed.

Institution of any therapy in response to detection of MRD, including withdrawal of immunosuppressive therapy or treatment with hypomethylating agents, is considered evidence of relapse regardless of whether the criteria described above are met.

In some embodiments, the present invention provides an article of manufacture, a composition or kit comprising a packaging material and umbilical cord blood cell fractions comprising:

(i) a first blood cell fraction suitable for transplantation into a subject in need thereof comprising CD133+/CD34+ selected cord blood cells ex-vivo cultured under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM; and (ii) a second, uncultured, unselected blood cell fraction suitable for transplantation into a subject in need thereof comprising CD133/CD34 negative cells, wherein said packaging material comprises a label or package insert indicating that said first and second umbilical cord blood cell populations are for treating a hematological disease in a subject in need thereof.

In some embodiments, the article of manufacture, composition or kit of the present invention further comprises instructions for administering the (i) first blood cell fraction suitable for transplantation into a subject in need thereof comprising CD133+/CD34+ selected cord blood cells and (ii) the second, uncultured, unselected blood cell fraction suitable for transplantation into a subject in need thereof comprising CD133/CD34 negative cells to a subject in need thereof.

In some embodiments of the article of manufacture, composition or kit of the present invention, the (i) first blood cell fraction suitable for transplantation into a subject in need thereof comprising CD133+/CD34+ selected cord blood cells comprises at least $8\times10^8$ total viable cells. In some embodiments, the first CD133+/CD34+ selected cord blood fraction comprises at least $10\times10^8$ total viable cells, at least $15\times10^8$ total viable cells, at least $20\times10^8$ total viable cells or at least $25\times10^8$ total viable cells. In some embodiments of the article of manufacture, composition or kit of the present invention, the (ii) second, uncultured, unselected blood cell fraction suitable for transplantation into a subject in need thereof comprising CD133/CD34 negative cells comprises $4\times10^8$ total viable cells. In some embodiments, second, uncultured, unselected blood cell fraction suitable for transplantation into a subject in need thereof comprising CD133/CD34 negative cells comprises at least $6\times10^8$ total viable cells, at least $8\times10^8$ total viable cells, at least $10\times10^8$ total viable cells or at least $15\times10^8$ total viable cells.

In some embodiments of the article of manufacture, composition or kit of the present invention, the (i) first blood cell fraction suitable for transplantation into a subject in need thereof comprising CD133+/CD34+ selected cord blood cells and the (ii) second, uncultured, unselected blood cell fraction suitable for transplantation into a subject in need thereof comprising CD133/CD34 negative cells are provided as cryopreserved cord blood cell fractions.

Selected cell populations of the present invention can be provided per se, along with the culture medium containing same, isolated from the culture medium, and combined with a pharmaceutically acceptable carrier as well as with additional agents which may promote cell engraftment and/or organ function (e.g., immunosuppressing agents, antibiotics, growth factor). Hence, cell populations of the invention can be administered in a pharmaceutically acceptable carrier or diluent, such as sterile saline and aqueous buffer solutions. The use of such carriers and diluents is well known in the art.

Compositions of the present invention may, if desired, be presented in a pack or dispenser device, such as an FDA-approved kit or article of manufacture, which may contain one or more unit dosage forms containing the active ingredient (e.g., cells). The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

The cells prepared according to the methods of the present invention can be administered to the subject per se, or in a pharmaceutical composition where it is mixed with suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient.

Techniques for formulation and administration of drugs may be found in the latest edition of "Remington's Pharmaceutical Sciences," Mack Publishing Co., Easton, Pa., which is herein fully incorporated by reference.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g. expanded CD133+/CD34+ cells) effective to prevent, alleviate, or ameliorate symptoms of a disorder (e.g., leukemia) or prolong the survival of the subject being treated.

Determination of a therapeutically effective amount is well within the capability of those skilled in the art, especially in light of the detailed disclosure provided herein.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity and responsiveness of the condition to be treated, dosing can be of a single or a plurality of administrations. The amount of a composition to be administered will, of course, be dependent on the subject being treated, the severity of the affliction, the manner of administration, the judgment of the prescribing physician, etc.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of treating a hematological disease in a subject in need thereof, the method comprising:
   (a) separating a single umbilical cord blood unit suitable for transplantation into said subject into (i) a first, selected blood cell fraction comprising CD133+/CD34+ selected cells and (ii) a second, unselected blood cell fraction comprising CD133/CD34 negative cells;
   (b) ex vivo culturing said first blood cell fraction comprising CD133+/CD34+ selected cells under conditions allowing for cell proliferation, said conditions comprising providing nutrients, serum and a combination of cytokines including each of stem cell factor, thrombopoietin, FLt3 ligand and IL-6 and nicotinamide in an amount between 1.0 mM to 10 mM;
   (c) cryopreserving said ex-vivo cultured first, CD133+/CD34+ selected blood cell fraction and said uncultured second, unselected blood cell fraction from step (b),
   (d) thawing said ex-vivo cultured first selected and said uncultured second, unselected blood cell fractions, and
   (e) transplanting the thawed ex-vivo cultured first selected and uncultured second unselected blood cell fractions from step (d) into a subject in need thereof,
   thereby treating said hematological disease in said subject.

2. The method of claim 1, wherein said cryopreserved ex-vivo cultured first selected and said uncultured second, unselected blood cell fractions are thawed on the same day of transplantation.

3. The method of claim 1, wherein said cryopreserved ex-vivo cultured first selected and said uncultured second, unselected blood cell fractions are thawed and reconstituted in infusion solution and wherein said transplantation is affected by infusion in an infusion solution into said patient.

4. The method of claim 3, wherein said ex-vivo cultured first selected blood cell fraction is infused prior to said uncultured second, unselected blood cell fraction.

5. The method of claim 3, wherein said uncultured second, unselected blood cell fraction is infused prior to said ex-vivo cultured first selected blood cell fraction.

6. The method of claim 1, wherein said first ex-vivo cultured blood cell fraction comprises at least $8\times10^8$ total viable cells and said second uncultured blood cell fraction comprises at least $4\times10^8$ total viable cells.

7. The method of claim 1, wherein said hematological disease is a hematological malignancy selected from the group consisting of chronic myelogenous leukemia (CML), acute lymphoblastic leukemia (ALL), acute myelogenous leukemia (AML) and myelodysplastic syndrome (MDS).

8. The method claim 7 wherein the subject has received at least one treatment selected from the group consisting of:
   (a) myeloablative therapy or other conditioning regime prior to transplantation;
   (b) graft-versus-host disease (GvHD) prophylaxis regime prior to transplantation; and
   (c) graft-versus-host disease (GvHD) prophylaxis regime following transplantation.

9. The method of claim 1, wherein transplantation of said first ex vivo cultured CD133+/CD34+ blood cell fraction and said second uncultured CD133−/CD34− blood cell fraction decreases time from transplantation to neutrophil engraftment in said subject, when compared to transplantation of a single or double unit of unmanipulated cord blood.

10. The method of claim 9, wherein said neutrophil engraftment consists of achieving an absolute neutrophil count (ANC)$\geq 0.5\times 10^9$/L on 3 consecutive measurements on different days with subsequent donor chimerism ($\leq 10\%$ host cells by peripheral blood chimerism), on or before 42 days post transplant.

11. The method of claim 1, wherein transplantation of said first ex vivo cultured CD133+/CD34+ blood cell fraction and said second uncultured CD133−/CD34− blood cell fraction decreases time from transplantation to platelet engraftment in said subject, when compared to transplantation of a single or double unit of unmanipulated cord blood.

12. The method of claim 11, wherein transplantation of said first ex vivo cultured CD133+/CD34+ hematopoietic stem/progenitor blood cell fraction and said second uncultured CD133−/CD34− blood cell fraction increases the probability of platelet engraftment in said subject at 42 days post transplantation or decreases risk of non-engraftment by day 42 after transplantation in said subject when compared to transplantation of a single or double unit of unmanipulated cord blood.

13. The method of claim 1, wherein transplantation of said first ex vivo cultured CD133+/CD34+ blood cell fraction and said second uncultured CD133−/CD34− blood cell fraction decreases the risk of non-relapse mortality after transplantation in said subject, when compared to transplantation of a single or double unit of unmanipulated cord blood.

14. The method of claim 13, wherein transplantation of said first ex vivo cultured CD133+/CD34+ blood cell fraction and said second uncultured CD133−/CD34− blood cell fraction decreases the risk of non-relapse mortality at 210 days after transplantation or transplantation related mortality at 1 year.

15. The method of claim 1, wherein transplantation of the first ex vivo cultured CD133+/CD34+ blood cell fraction and said second uncultured CD133−/CD34− blood cell fraction decreases duration of hospitalization in said subject in the first 100 days post-transplantation by 5-30 days, when compared to transplantation of a single or double unit of unmanipulated cord blood.

16. The method of claim 1, wherein transplantation of the first ex vivo cultured CD133+/CD34+ blood cell fraction and said second uncultured CD133−/CD34− blood cell fraction decreases risk of grade 2/3 bacterial or invasive fungal infections post-transplantation in said subject, when compared to transplantation of a single or double unit of unmanipulated cord blood.

17. The method of claim 16, wherein transplantation of the first ex vivo cultured CD133+/CD34+ blood cell fraction and said second uncultured CD133−/CD34− blood cell fraction decreases risk of grade 2/3 bacterial or invasive fungal infections by 100 days post-transplantation in said subject, when compared to transplantation of a single or double unit of unmanipulated cord blood.

18. The method of claim 1, wherein transplantation of the first ex vivo cultured CD133+/CD34+ blood cell fraction and said second uncultured CD133−/CD34− blood cell fraction decreases risk of acute graft-versus-host disease grade III-IV in said subject at 100 days post transplantation, when compared to transplantation of a single or double unit of unmanipulated cord blood.

19. The method of claim 1, wherein transplantation of the first ex vivo cultured CD133+/CD34+ blood cell fraction and said second uncultured CD133−/CD34− blood cell fraction decreases risk of severe chronic graft-versus-host disease in said subject at 180 days post transplantation, when compared to transplantation of a single or double unit of unmanipulated cord blood.

20. The method of claim 1, wherein said first and second blood cell fractions are co-administered in conjunction with an additional treatment for hematological disease.

21. The method of claim 20, wherein said additional treatment is selected from the group consisting of immunosuppressive treatment, chemotherapy and radio-therapy.

22. The method of claim 1, wherein said single umbilical cord blood unit suitable for transplantation is characterized by the following pre-cryopreservation parameters:
   (i) at least $8\times 10^6$ total CD34+ cells;
   (ii) HLA-matched at at least 4 out of 6 HLA class I (HLA-A and HLA-B, low resolution) and HLA class II (HLA-DRB1, high resolution) loci with said subject;
   (iii) about $1.8\times 10^9$ to about $3.0\times 10^9$ pre-cryopreserved total nucleated cells, and
   (iv) about $1.5\times 10^7$ to about $3.0\times 10^7$ pre-cryopreserved total nucleated cells per kilogram subject weight.

23. The method of claim 1, wherein the amount of nicotinamide is 2.5 mM to 5.0 mM.

24. The method of claim 1, wherein the amount of nicotinamide is 2.5 mM.

25. The method of claim 1, wherein the amount of nicotinamide is 5.0 mM.

* * * * *